(12) United States Patent
Morris

(10) Patent No.: US 6,491,656 B1
(45) Date of Patent: *Dec. 10, 2002

(54) INTEGRATED CASSETTE FOR CONTROLLING FLUID HAVING AN INTEGRAL FILTER

(75) Inventor: Livingston B. Morris, Devon, PA (US)

(73) Assignee: Therakos, Inc., Exton, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/975,688

(22) Filed: Nov. 21, 1997

Related U.S. Application Data

(60) Provisional application No. 60/031,907, filed on Nov. 22, 1996, now abandoned.

(51) Int. Cl.$^7$ ............... A61M 35/00; B01D 63/00; C02F 1/44
(52) U.S. Cl. ............ 604/6.09; 604/6.1; 604/5.01; 210/321.62; 210/321.75; 210/321.72; 210/257.2
(58) Field of Search .................. 604/4–6, 4.01, 604/5.01, 6.01–6.04, 6.07, 6.08, 6.09, 6.1, 6.11, 19, 27–31, 34, 66–67; 128/DIG. 12, 13; 417/279, 458, 479, 442, 448, 474–75, 477.2, 477.9; 137/613, 454.2, 454.4, 315.05, 546, 861, 863; 210/739, 741, 321.6, 321.62, 321.71–321.72, 321.75, 500.1, 503, 252, 256–88, 257.1–257.2, 258–62; 422/44–48

(56) References Cited

U.S. PATENT DOCUMENTS 4,056,476 A * 11/1977 Mouwan et al. ............ 210/446

| 4,265,601 A | | 5/1981 | Mandroian |
|---|---|---|---|
| 4,392,791 A | | 7/1983 | Mandroian |
| 4,713,171 A | * | 12/1987 | Polaschegg ............ 210/110 |
| 5,174,894 A | * | 12/1992 | Ohsawa et al. ............ 210/86 |
| 5,178,182 A | | 1/1993 | Kamen |
| 5,350,357 A | * | 9/1994 | Kamen et al. ............ 604/29 |
| 5,634,896 A | * | 6/1997 | Bryant et al. |
| 5,863,421 A | * | 1/1999 | Peter, Jr. et al. |

FOREIGN PATENT DOCUMENTS

| FR | 2513884 | 4/1983 |
|---|---|---|
| GB | 2176717 | 1/1987 |
| WO | WO 8402473 | 7/1984 |
| WO | WO 9315777 | 8/1993 |
| WO | WO 98/22165 | 5/1998 |

OTHER PUBLICATIONS

International Search Report Application No. PCT/US97/21656 dated Mar. 12, 1998.

* cited by examiner

Primary Examiner—Angela D. Sykes
Assistant Examiner—Patricia Bianco

(57) ABSTRACT

An apparatus controls movement of fluids during an extracorporeal blood treatment session. A hollow cassette enclosure has a plurality of fluid input ports for receiving fluids into the enclosure and a plurality of fluid output ports for expelling fluids from the enclosure. Internal fluid passageways disposed within the hollow enclosure are provided for coupling together the fluid input ports, and the fluid output ports. At least one internal valve is disposed within the hollow enclosure for controlling movement of the fluid within the hollow enclosure. A filter is integrated into the cassette to filter the blood passing therethrough.

9 Claims, 30 Drawing Sheets

PRIME A/C
& PATIENT LINES

FIG. 6 PRIMING BACK SALINE UP TO ACCESS

PRIMING

PRIMING

PRIMING

PRIMING

PRIMING

PRIMING

COLLECTION

BUFFY COAT
COLLECTION

EMPTY BOWL

RED CELL/PLASMA RETURN
REPEAT STEPS 9 THRU 12 6 TIMES

RINSE CENTRIFUGE

RINSE PLASMA / RETURN BAG

FIG. 19  RETURN RINSE

LIGHTS ON
RINSE RECIRC.
LOOP

LIGHTS ON;
BUFFY COAT
RECIRC.

TREATED CELLS RETURN

TREATED CELLS RETURN

RINSE TREATMENT CHAMBER

RINSE RECIRCULATION BAG

RETURN RINSE

DELIVER SALINE

PRIME A/C
& PATIENT LINES

INTEGRATED CASSETTE FOR CONTROLLING FLUID HAVING AN INTEGRAL FILTER

This application claims priority from U.S. Application Ser. No. 60/031,907 filed Nov. 22, 1996, now abandoned.

FIELD OF THE INVENTION

The present invention relates generally to systems for controlling fluid flow. More particularly, the present invention relates to systems for infusing fluids in and withdrawing fluids from patients undergoing medical care.

BACKGROUND

Several treatments for disease require the removal of blood from a patient, processing the one or more components of the blood and return of the processed components for a therapeutic effect. Those extracorporeal treatments require systems for safely removing blood from the patient, separating it into components, where necessary, and returning the blood to the patient.

Photopheresis is one treatment involving the separation of white cells from the blood, addition of a photoactivatable drug, and U.V. irradiation of the white cells before re-infusion to the patient. In known photopheresis systems, such as system 100 shown in FIG. 1, blood fluids are pumped by peristaltic roller pumps 110. In system 100, a complex tubing set is used to couple a patient 120 to an extracorporeal blood treatment system which includes a cell separator 130, a white blood cell photoactivation chamber 140, a saline bag 150a, an anti-coagulant bag 150b and a waste bag 150c. Valves 160, bubble chambers 170, air detectors 180, and pressure sensors 190 are interconnected to the tubing set for monitoring and controlling fluid flow within the system. Complex tubing sets, such as that shown in FIG. 1, have the potential to cause cell damage under high outlet pressure conditions. Blood has also been pumped with discrete pump chambers and valves which also require complex tubing sets. Such discrete pump chambers and valves are considered to be less damaging to cells under high outlet pressures.

A very real advancement in photopheresis systems would result if the size and complexity of the tubing in systems such as that shown in FIG. 1 could be reduced, even at the cost of a more complex blood driving system, since the blood driving system represents permanent reusable equipment, whereas the tubing set must be replaced or disposed of after each treatment session. A similar result has been accomplished with peritoneal dialysis systems, where the flow of dialysate is controlled entirely with diaphragm pumps and valves driven by air pulses delivered to a molded cassette through a plastic membrane. See for instance several patents by Dean Kamen, including U.S. Pat. No. 5,178,182, issued Jan. 12, 1993 and U.S. Pat. No. 5,634,896 issued Jun. 3, 1997, which are incorporated herein by reference.

The cassette contains all components of a previously complex tubing set, except for the lines to the patient and short delivery lines from the dialysate containers. The air pulses delivered to the cassette are controlled by continually analyzing the pressure changes in the air delivered to the diaphragm pumps, processing the pressure changes through a computer, and making continual corrections as a result. The resulting peritoneal dialysis system is able to accurately measure the fluid delivered, but is unable to provide a fixed steadiness of flow rate. In contrast to peritoneal dialysis systems, systems such as photopheresis systems, which involve continuous blood cell separation, require both a very steady flow rate, as well as the ability to control the fluid flow rate. Furthermore, such a system may tend to promote clotting, hemolysis and cell lysis when pumping blood, as opposed to its intended fluid, dialysate which contains no cellular components.

SUMMARY OF THE INVENTION

An apparatus according to the present invention controls movement of fluids during an extracorporeal blood treatment session. It comprises a hollow enclosure having a plurality of fluid input ports for receiving the fluids into the enclosure and a plurality of fluid output ports for expelling fluids from the enclosure. Internal fluid passageways within the hollow enclosure couple together the fluid input ports, and the fluid output ports. At least one internal valve is disposed within the hollow enclosure and connected to at least one of the internal fluid passageways for controlling movement of the fluid within the hollow enclosure during the extracorporeal blood treatment session. A filter in the hollow enclosure filters the fluids.

Preferably, the filter comprises a first chamber and a second chamber within the enclosure which are separated from each other by a filter media, having a pore size of 200 to 400 microns, and most preferably about 200 microns. A filter media of woven mesh, such as a woven polyester such as DACRON brand is preferred. One or both of the filter chambers can be partially formed by an elastomeric membrane material outer surfaces of the hollow enclosure. Preferably, some means is provided to evacuate air from the filter chambers.

A method according to the present invention for controlling movement of fluids during an extracorporeal blood treatment comprises the steps of: extracting blood from a patient and admitting the blood into a hollow enclosure having a plurality of fluid input ports for receiving the blood into the enclosure, a plurality of fluid output ports for expelling the blood from the enclosure and a plurality of internal fluid passageways disposed within the hollow enclosure for coupling together the fluid input ports, the fluid output ports; directing flow of the blood through selected ones of the fluid passageways with at least one internal valve disposed within the hollow enclosure; and filtering the blood through a filter in the hollow enclosure.

Preferably, the first chamber is at least partially formed of a first layer of flexible membrane material disposed on a first outer surfaces of the hollow enclosure and the method further comprises the step of measuring the pressure in the first chamber by measuring the pressure against the flexible membrane. The blood is preferably returned to the patient from the hollow enclosure, and the filtering step preferably closely precedes the step of returning the blood to the patient so as to reduce the possibility of a clot forming in the enclosure and returning to the patient.

BRIEF DESCRIPTION OF THE DRAWINGS

In order that the manner in which the above-recited and other advantages and objects of the invention are obtained and can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings, wherein.

DETAILED DESCRIPTION OF THE INVENTION

Figure 1:
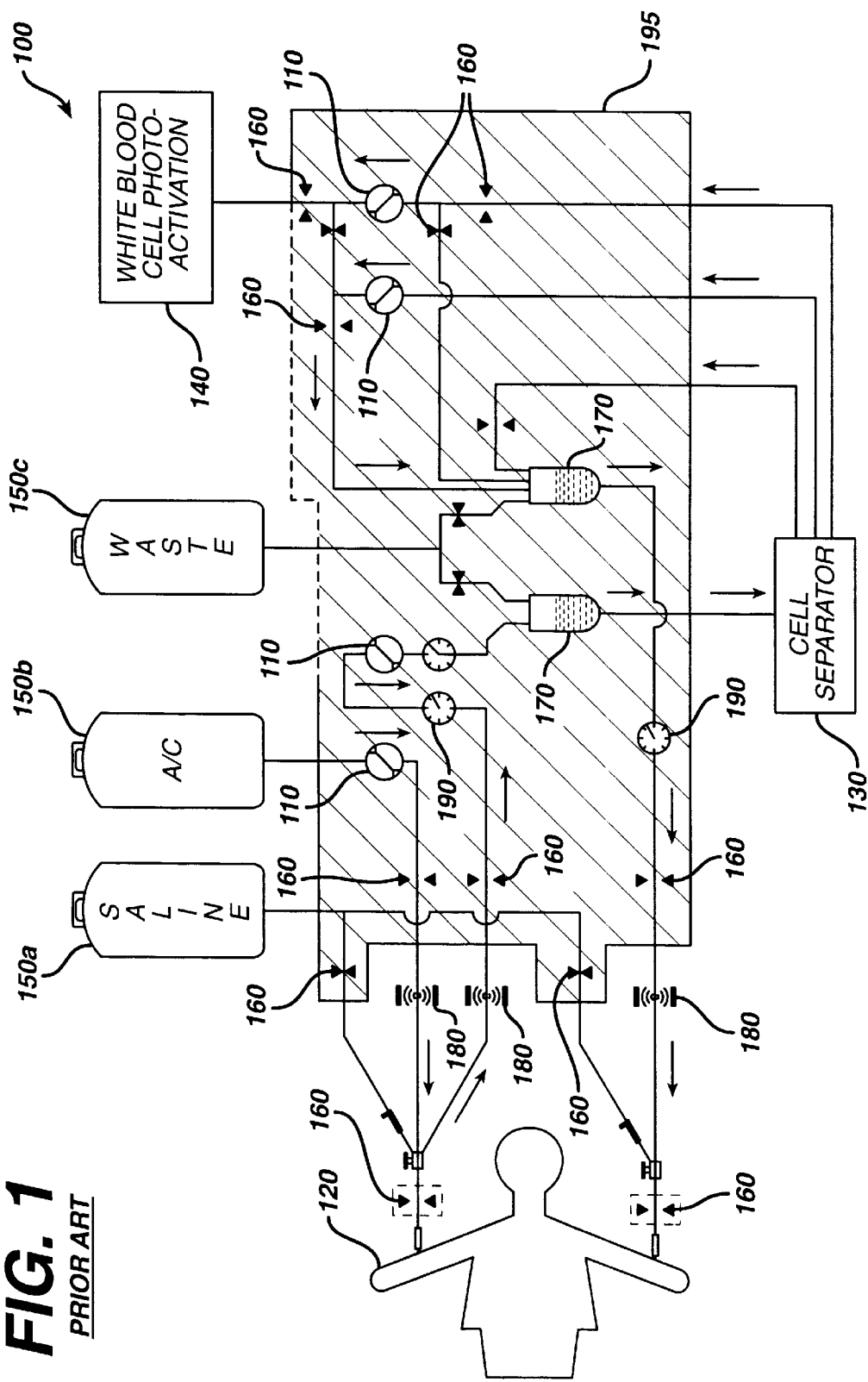
FIG. 1 is a block diagram showing a prior art photopheresis system.
Figure 2:
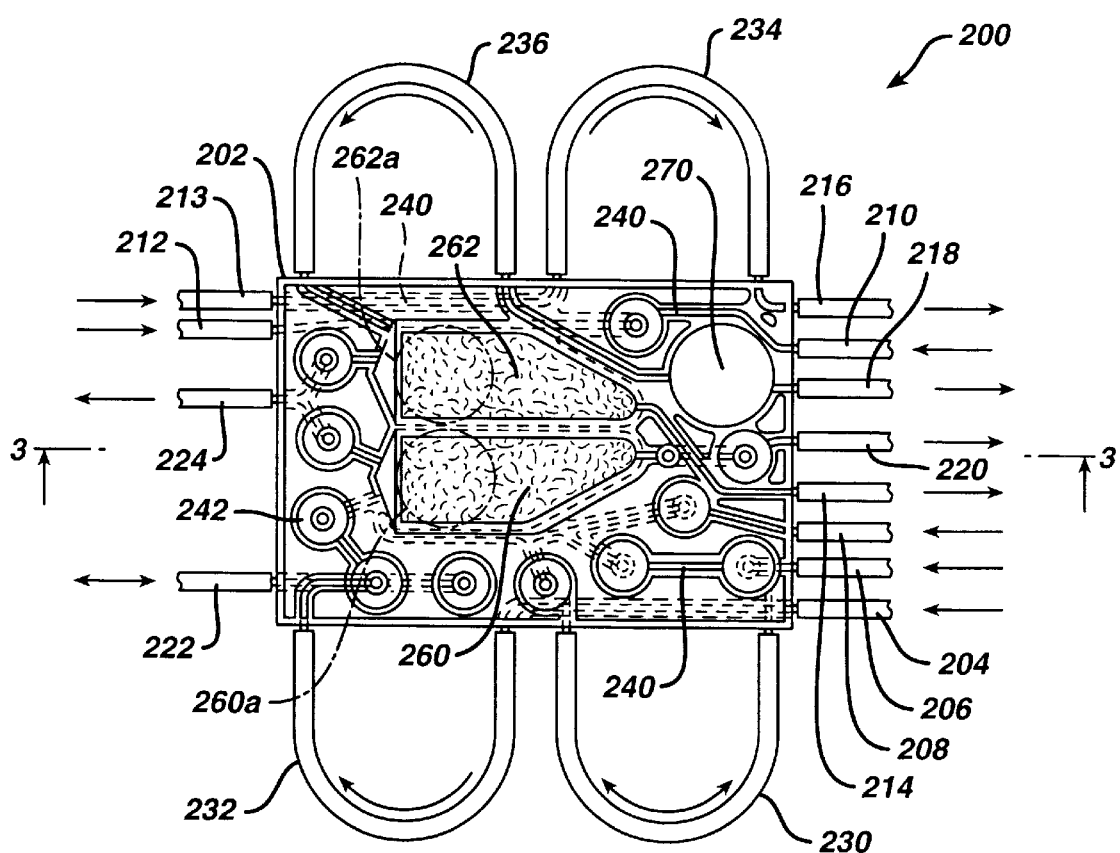
FIG. 2 is a bottom view of an integrated disposable cassette for valving, pumping and controlling the movement of blood fluids during a photopheresis treatment session, in accordance with a preferred embodiment of the present invention.

Referring now to FIG. 2, there is shown a bottom (or actuator) side view of an integrated disposable cassette 200 for valving, pumping and controlling the movement of blood fluids during a photopheresis treatment session. Cassette 200 is formed of a hollow injection-molded enclosure 202 having fluid input ports 204, 206, 208, 210, 212 and 214 for receiving fluids into enclosure 202, and fluid output ports 214, 216, 218, 220 and 224 for expelling fluids from cassette 200. Input/output port 222 is provided for both receiving fluid into and expelling fluid from cassette 200. As explained more fully below, these fluid input and output ports couple cassette 200 to a patient being treated, as well as devices in the photopheresis treatment system such as a cell separator 130 and a photoactivation chamber 140 and bags, such as bags 150a, 150b and 150c, containing saline, anticoagulation fluid, and waste fluid, respectively. Significantly, all of the tubing, valves, sensors, drip chambers and pumps shown within box 195 (FIG. 1) are implemented within disposable cassette 200.

During a photopheresis treatment session, cassette 200 is snapped into a permanent cassette actuation or driving unit (not shown), and the input and output ports from cassette 200 are coupled to various treatment devices and to a patient. The details of such couplings are explained more fully below. At the conclusion of the treatment session, the cassette 200 is removed from the permanent cassette actuation unit and thereafter is discarded.

Referring still to FIG. 2, ports 204, 206, 208 and 214 are provided for coupling disposable cassette 200 to a centrifuge or cell separator. More specifically, output port 214 is provided for delivering whole blood from cassette 200 to the centrifuge, and input ports 204, 206 and 208 are respectively provided for returning plasma, white blood cells (WBC), and red blood cells (RBC) to cassette 200. Ports 204, 206, 208 and 214 are preferably coupled to the centrifuge with disposable tubing (not shown). Similarly, ports 210, 216, 218 and 220 are provided for coupling disposable cassette 200 to a patient. More specifically, input port 218 is provided for delivering untreated blood from the patient to cassette 200, and output ports 216, 210 and 220 are respectively provided for returning treated blood, saline and an anticoagulant from cassette 200 to the patient. Ports 210, 216, 218 and 220 are preferably coupled to the patient with disposable tubing (not shown). Input/output port 222 is provided for delivering untreated WBC from cassette 200 to a photoactivation chamber and for returning treated WBC from the photoactivation chamber to cassette 200. Again, port 222 is preferably coupled to cassette 200 with disposable tubing (not shown). Finally, input ports 212 and 213 are respectively provided for receiving saline and anticoagulant fluid from storage bags (not shown) to cassette 200, and output port 224 is provided for delivering waste fluid expelled from cassette 200 to a waste collection bag (also not shown).

In one preferred embodiment of the present invention, four roller pumps are used to drive the blood fluids described above through the interior of cassette 200. The roller pumps are part of the permanent cassette actuation or driving unit which cassette 200 is snapped into at the inception of each treatment session. More specifically, roller pump tubes 230, 232, 234, and 236 engage the roller pumps in the permanent cassette driving unit when cassette 200 is snapped into the permanent cassette driving unit. Each roller pump tube 230, 232, 234 and 236 is coupled to cassette 200 by two ports which respectively receive and/or deliver blood fluids from and to cassette 200. In the preferred embodiment, roller pump tube 230 is provided for driving WBC through cassette 200; roller pump tube 232 is provided for driving plasma through cassette 200; roller pump tube 234 is provided for driving anti-coagulant fluid through cassette 200; and pump tube 236 is provided for driving untreated blood received from the patient through cassette 200.

Figure 4:
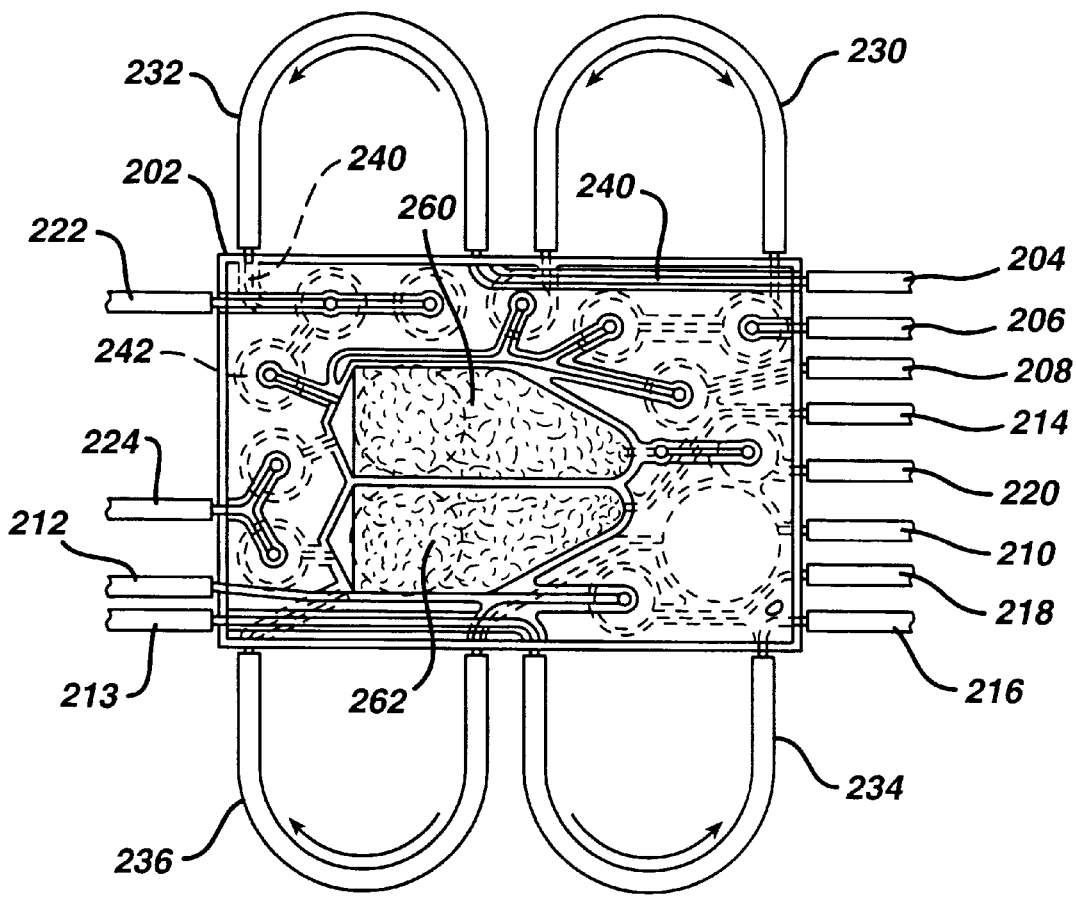
FIG. 4 is a top view of the integrated disposable cassette shown in FIG. 2.

Injection-molded enclosure 202 includes internal fluid passageways 240 which are disposed within the interior of cassette 200. As shown in FIGS. 2 and 4, interior fluid passageways 240 function to couple together fluid ports 204, 206, 208, 210, 212, 216, 218, 220, 222, 224 and roller pump tubes 230, 232, 234 and 236 throughout the interior of cassette 200. Passageways 240 are preferably integral with hollow-enclosure 202, and enclosure 202 and passageways 240 are therefore preferably formed from a singular injection-molded piece of plastic material.

Figure 3:
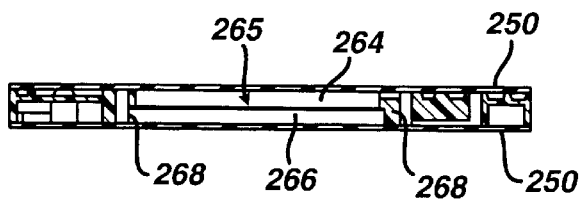
FIG. 3 is a cross-sectional view of the integrated disposable cassette shown in FIG. 2.

Internal diaphragm valves 242 are disposed throughout the interior of cassette 200. Valves 242 are provided for controlling the movement of the blood fluids that travel through internal passageways 240 during a photopheresis treatment session. Valves 242 are preferably formed as part of the singular injected-molded piece of plastic material used to form enclosure 202 and passageways 240. An elastomeric membrane 250 (shown in FIG. 3) covers the upper and lower surfaces of enclosure 202. During a photopheresis treatment session, solenoid valves disposed within the permanent cassette driving unit transmit controlled air or liquid pulses to diaphragm valves 242 through membrane 250 in order to open or close each valve 242. Alternatively, solenoid valves disposed with the permanent cassette driving unit could couple directly to membrane 250 and thereby directly drive valves 242 without any intermediate driving air or liquid.

A pair of drip chambers (filters) 260, 262 are disposed within the interior of enclosure 202. As shown more clearly in FIG. 3, each drip chamber is formed of compartments 264 and 266 which are separated by a mesh 265. The mesh 265 preferably comprises woven polyester, such as DACRON™ brand, and has a pore size of between 200 and 400 microns, with about 200 microns being preferred. Each compartment 264, 266 is sealed on one side by membrane 250. In addition, each compartment 264, 266 is connected to an internal fluid passageway 240 within enclosure 202. The walls 268 which form compartments 260, 262 can be formed as part of the singular injected-molded piece of plastic material used to form enclosure 202, passageways 240 and valves 242, or can receive an insert, such as a nylon insert (not shown) with the filter mesh 265 attached thereto for easy placement of the mesh 265 during construction of the enclosure 202. In the preferred embodiment of the present invention, drip chamber 260 is used for filtering treated blood before it is returned to the patient through outport 220 thereby to lessen the opportunity to return clots to the patient, chamber 262 is used for filtering whole blood before it is delivered to a centrifuge through output port 214.

By monitoring the position of the membrane 250 used to form drip chambers 260, 262, the permanent cassette driving device can monitor the pressures of the fluids in drip chambers 260, 262. Thus, in the preferred embodiment, pressure sensors are located on the permanent cassette driving device opposite locations 260a and 262a for monitoring the pressures inside drip chambers 260 and 262. In addition, a pressure sensor is preferably located on the permanent cassette driving device opposite location 270 for monitoring the pressure of untreated blood received from the patient through input port 218.

The enclosure 202 is preferably oriented in a vertical plane during use, with the port 224 facing upwardly. If air bubbles get into the blood flow therethrough, they may accumulate in the filter compartments 264 and 266. Excessive air therein reduces the area of the mesh 265 in contact with the blood and thus the efficiency of the filtering process. Therefore, it may be desirable to provide some means to evacuate air from the compartments 264 and 266 during the filtering process. For instance, the outlet from the downstream compartment can be placed at an upper location thereof to promote passing air thereout. More active measures may also be employed. For instance, an opening (not shown) may be provided for venting accumulated air, the opening being controlled by a valve, such as one of the membrane valves. The expelled air can be vented to atmosphere or routed along with perhaps some blood to a location having an air space such as a plasma holding bag, such as the plasma bag 314 (see FIG. 5).

Figure 5:
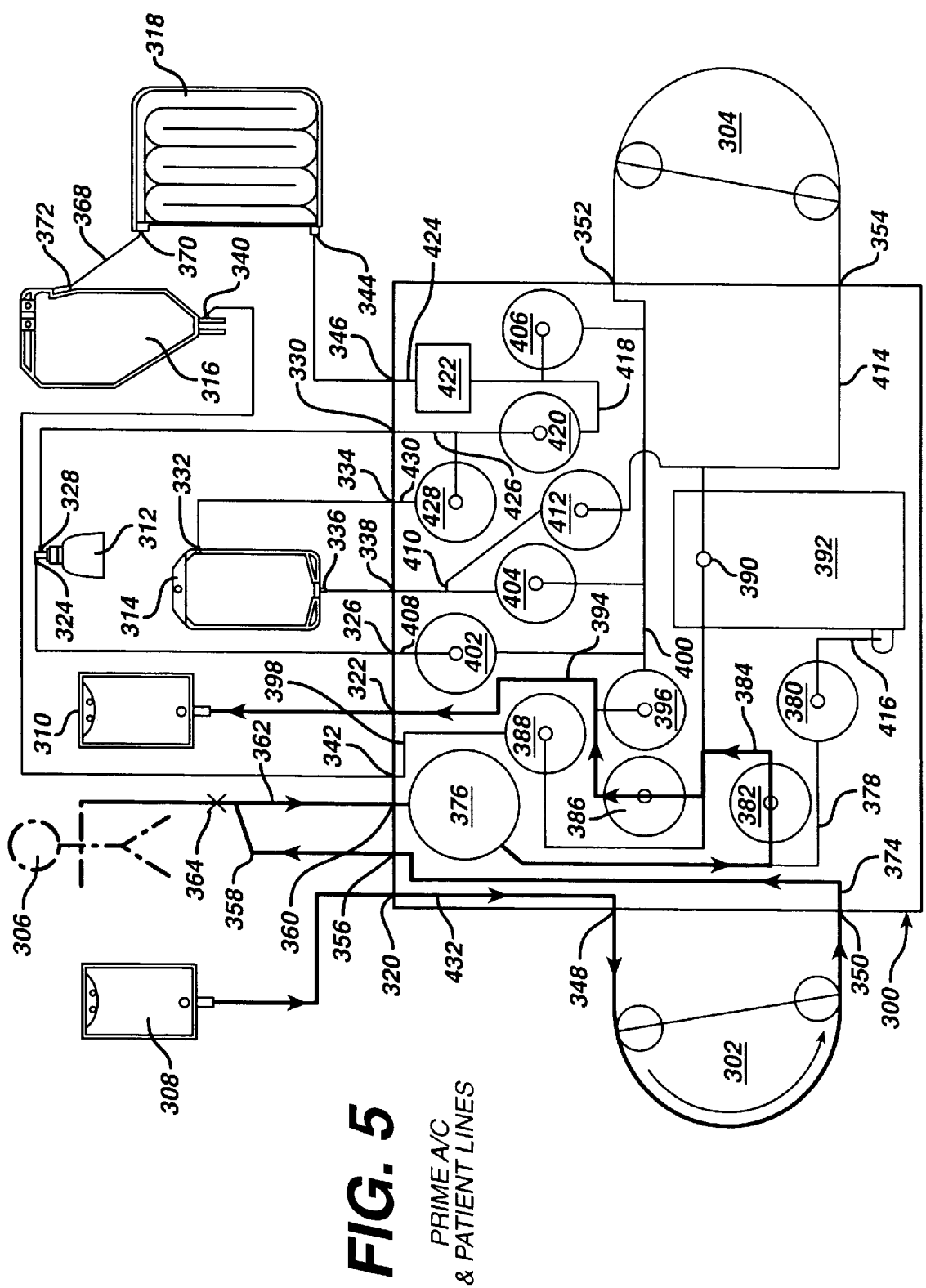
FIGS. 5 to 27 show in schematic form an alternative embodiment of an extracorporeal blood treatment system according to the invention, including the steps of performing such treatment.
Figure 6:
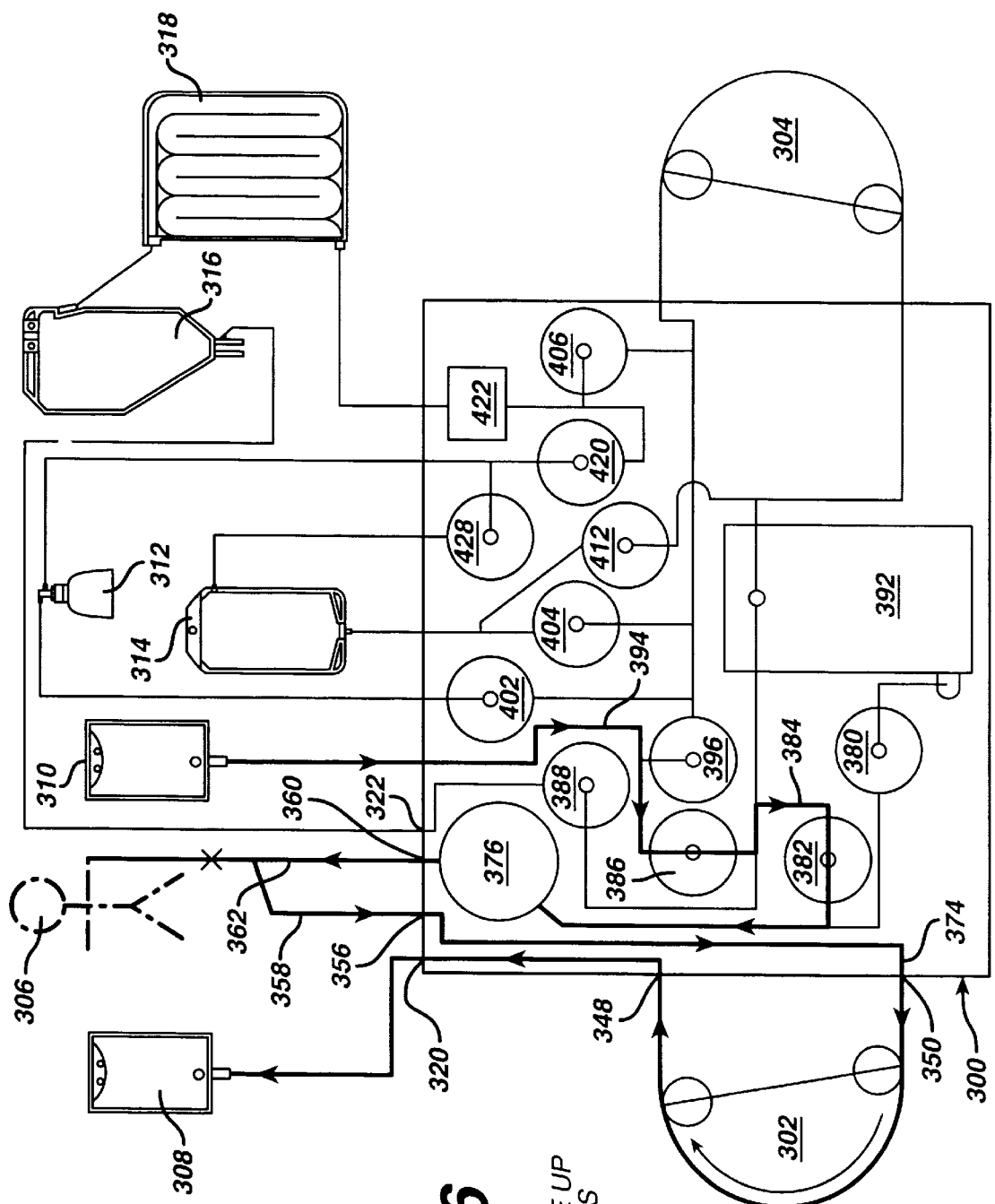
Figure 7:
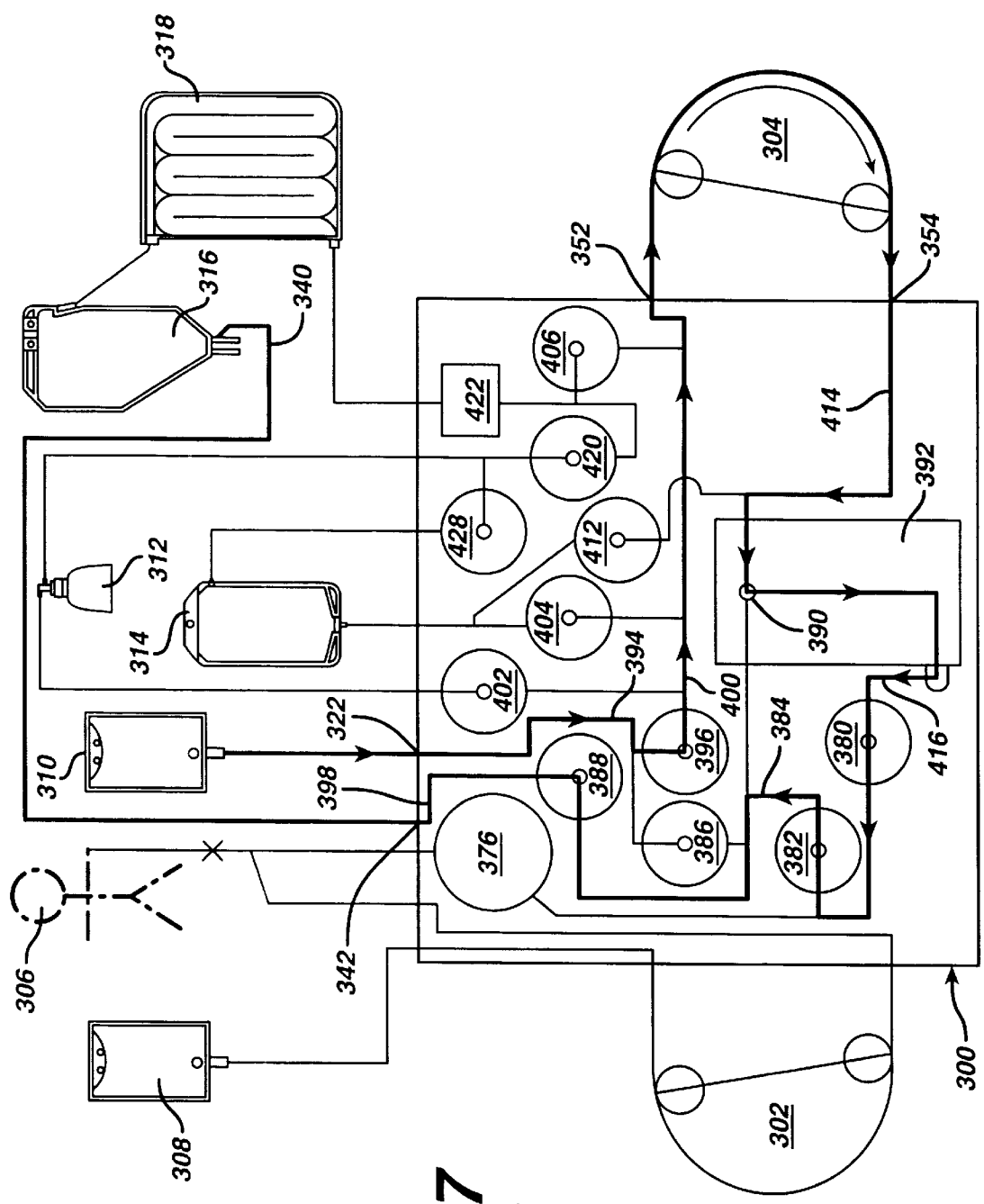
Figure 8:
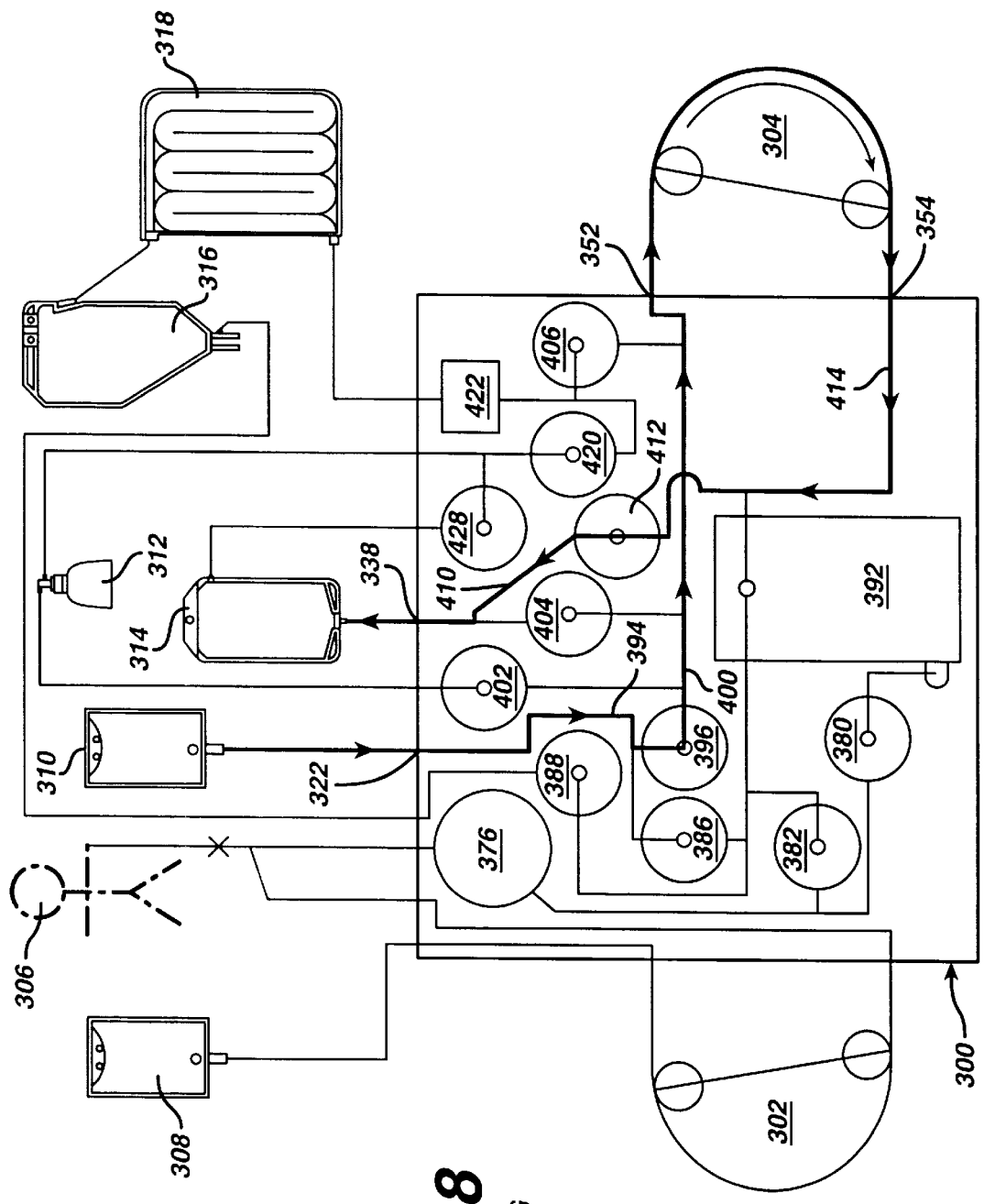
Figure 9:
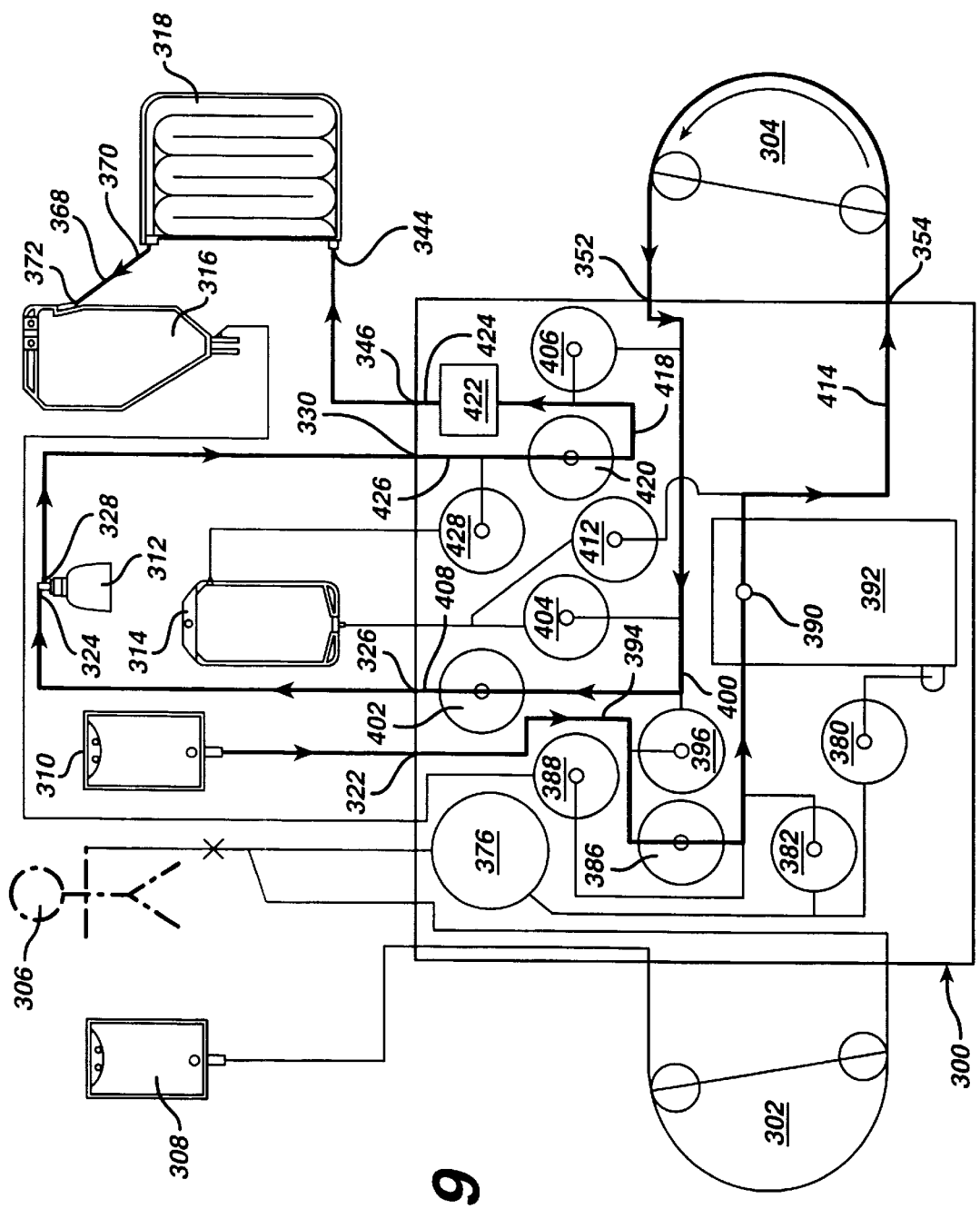
Figure 10:
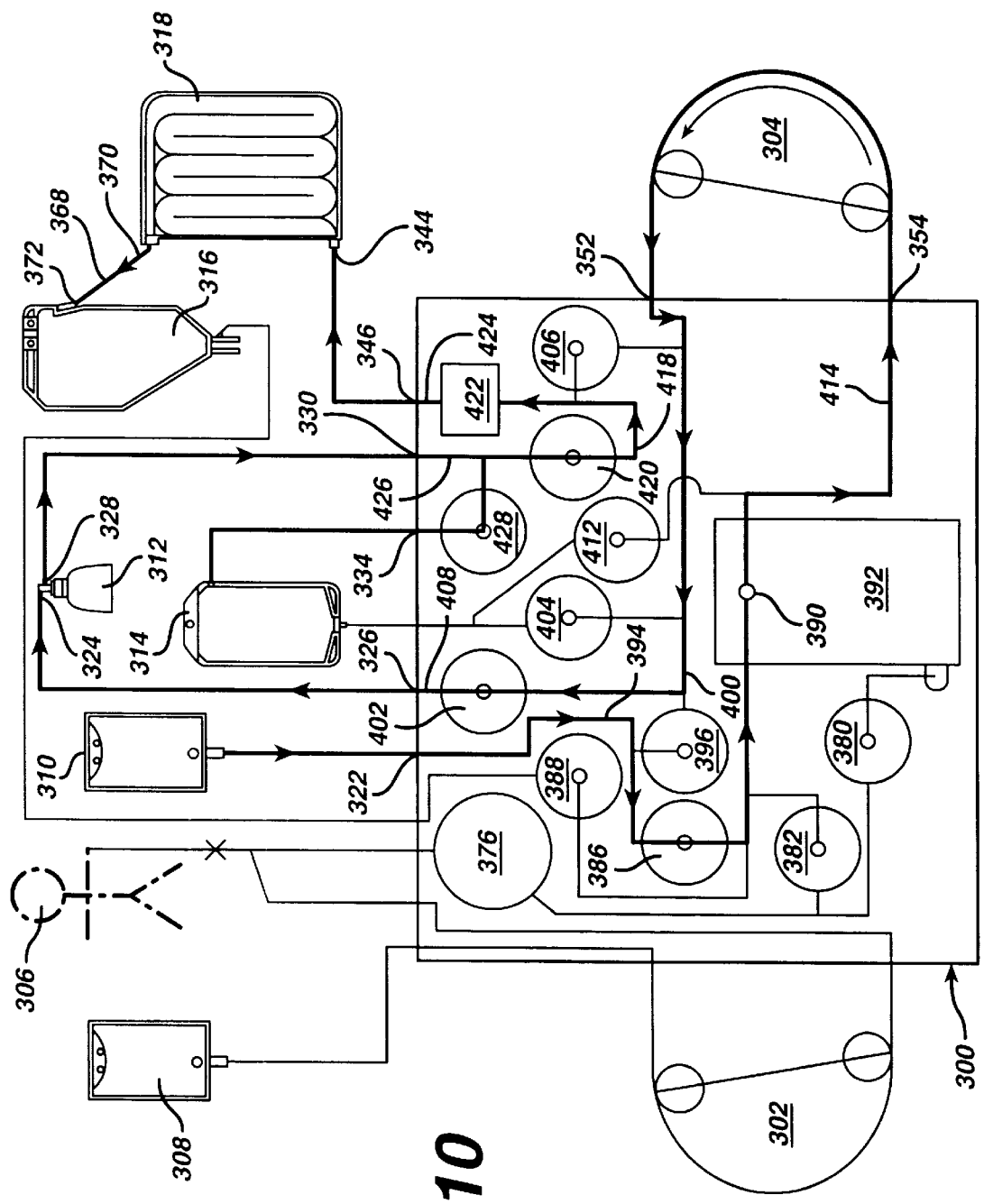
Figure 11:
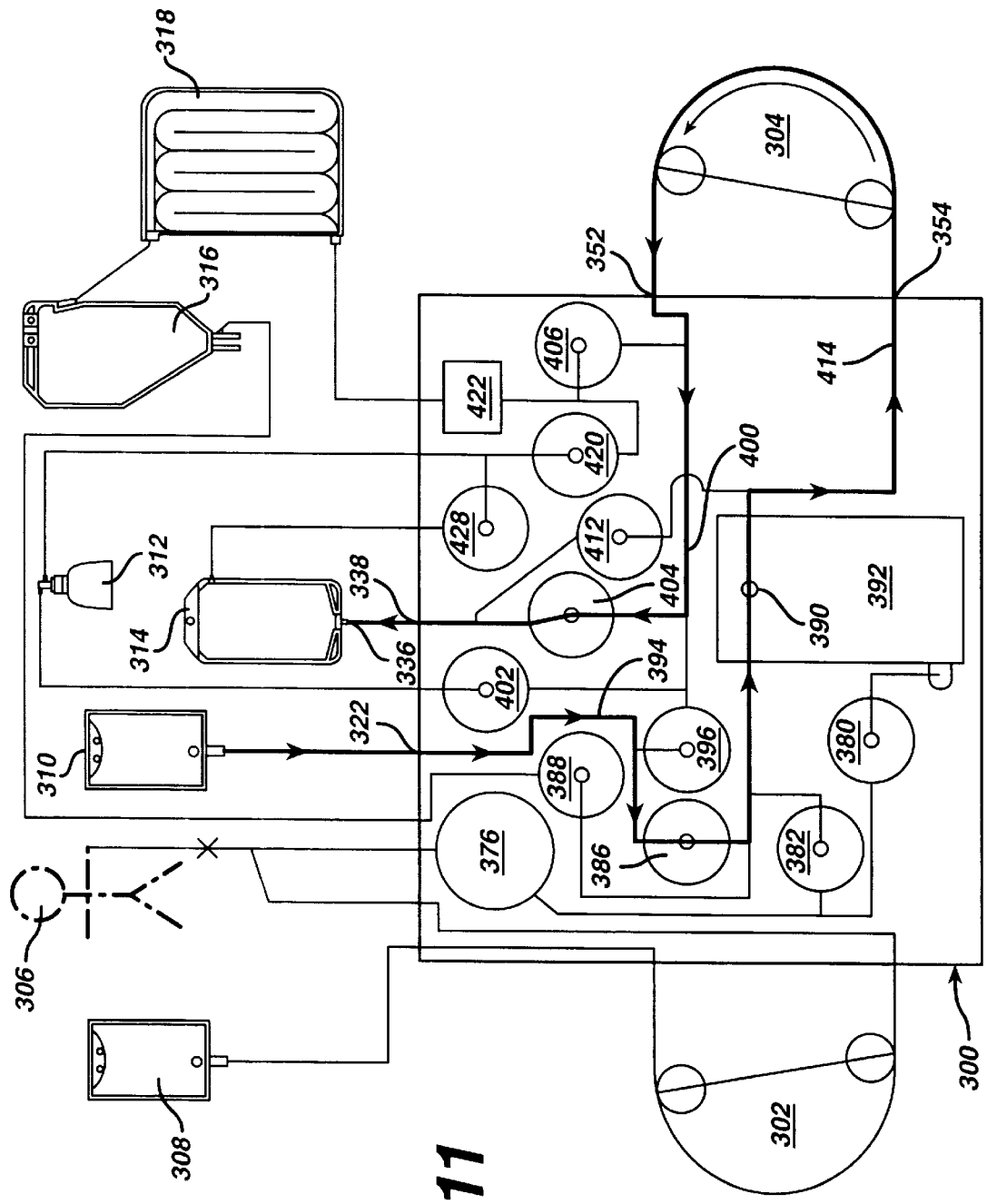
Figure 12:
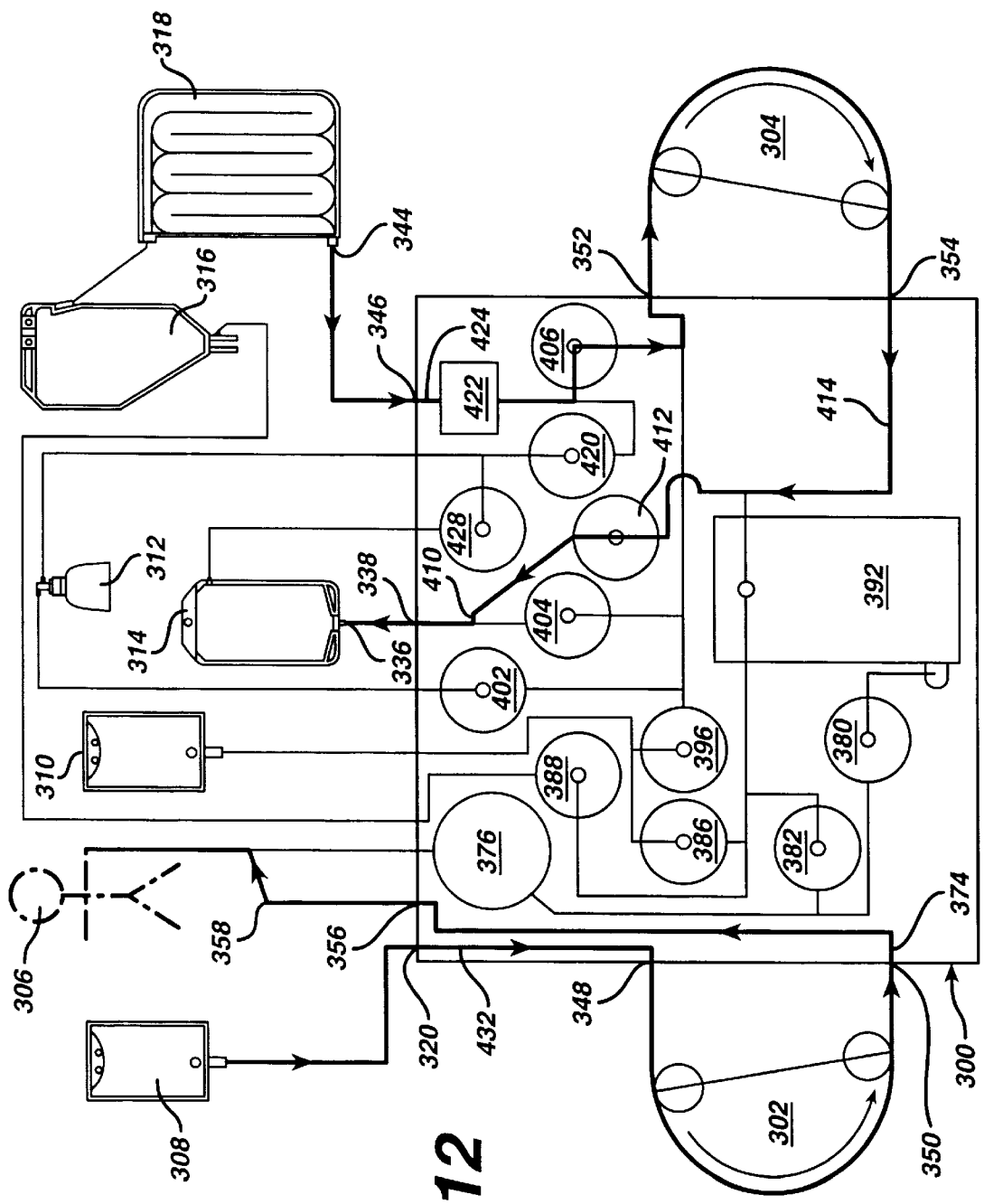

FIG. 5 shows an alternative embodiment of the invention in diagrammatic form. It employs a cassette 300 similar to that shown in FIGS. 2 to 4, but employing varying valving and porting. A first roller pump 302 pumps an anticoagulant fluid and a second roller pump 304 pumps blood from a patient 306. An anticoagulant bag 308, saline bag 310, centrifugal blood cell separator 312, plasma bag 314, recirculation bag 316 and light treatment chamber 318 connect to the cassette 300 at ports as follows: the anticoagulant bag 308 to an anticoagulant solution port 320, the saline bag 310 to a saline port 322, an inlet 324 on the cell separator 312 to a separator inlet port 326 and an exit 328 from the cell separator 312 to a separator exit port 330, an inlet 332 to the plasma bag 314 to a plasma inlet port 334, an exit 336 from the plasma bag 314 to a plasma exit port 338, an exit 340 from the recirculation bag 316 to a recirculation exit port 342, and an inlet 344 to the treatment chamber 318 to a treatment chamber inlet port 346. Additionally, ports 348 and 350 connect to the anticoagulant roller pump 302, ports 352 and 354 connect to the blood roller pump 304, port 356 connects to an anticoagulant exit line 358 and port 360 connects to the patient 306 via a patient access line 362. A clamp 364 in the patient access line is located upstream of where the anticoagulant line 358 connects to the patient access line 362. A line 368 connects an exit 370 from the treatment chamber 318 to an inlet 372 to the recirculation bag 316.

Internally of the cassette 300, passage 374 connects ports 350 and 356. A pressure sensor 376, comprising an electronic pressure transducer in contact with the membrane (not shown) of the cassette 300, connects to the patient access line port 360. From the sensor 376, passage 378 leads to a first valve 380 and second valve 382. As in FIGS. 2 to 4, each of the valves of cassette 300 comprise diaphragm valves with the cassette membrane acting to block and unblock a vertical passageway within a valve chamber. From the second valve 382, passage 384 leads to a third valve 386 and fifth valve 388. Passage 384 also leads to an inlet 390 of a filter 392, similar to the drip chamber filter 260 of the prior embodiment. Passage 394 connects the third valve 386 to the saline port 322 and to an eleventh valve 396. Passage 398 connects the fifth valve 388 to port 342. Passage 400 connects the eleventh valve 396 to a sixth valve 402, an eighth valve 404, a seventh valve 406 and to port 352 for the blood pump 304. Passage 408 connects the sixth valve 402 to port 326 and passage 410 connects the eighth valve 404 to port 338 and to a fourth valve 412. Passage 414 connects the fourth valve to port 354 for the blood pump 304 and to port 390 of the filter 392. Passage 416 leads from the filter 392 to the first valve 380. Passage 418 connects the seventh valve 406 to a ninth valve 420 and to a hematocrit detector 422 comprising a light emitting diode and photodector for detecting the presence of red blood cells passing through the detector 422. Passage 424 connects the hematocrit detector 422 to port 346 and passage 426 connects the ninth valve 420 to a tenth valve 428 and to port 330. Passage 430 connects the tenth valve 428 to port 334 and, finally, passage 432 connects port 320 to port 348.

Figure 13:
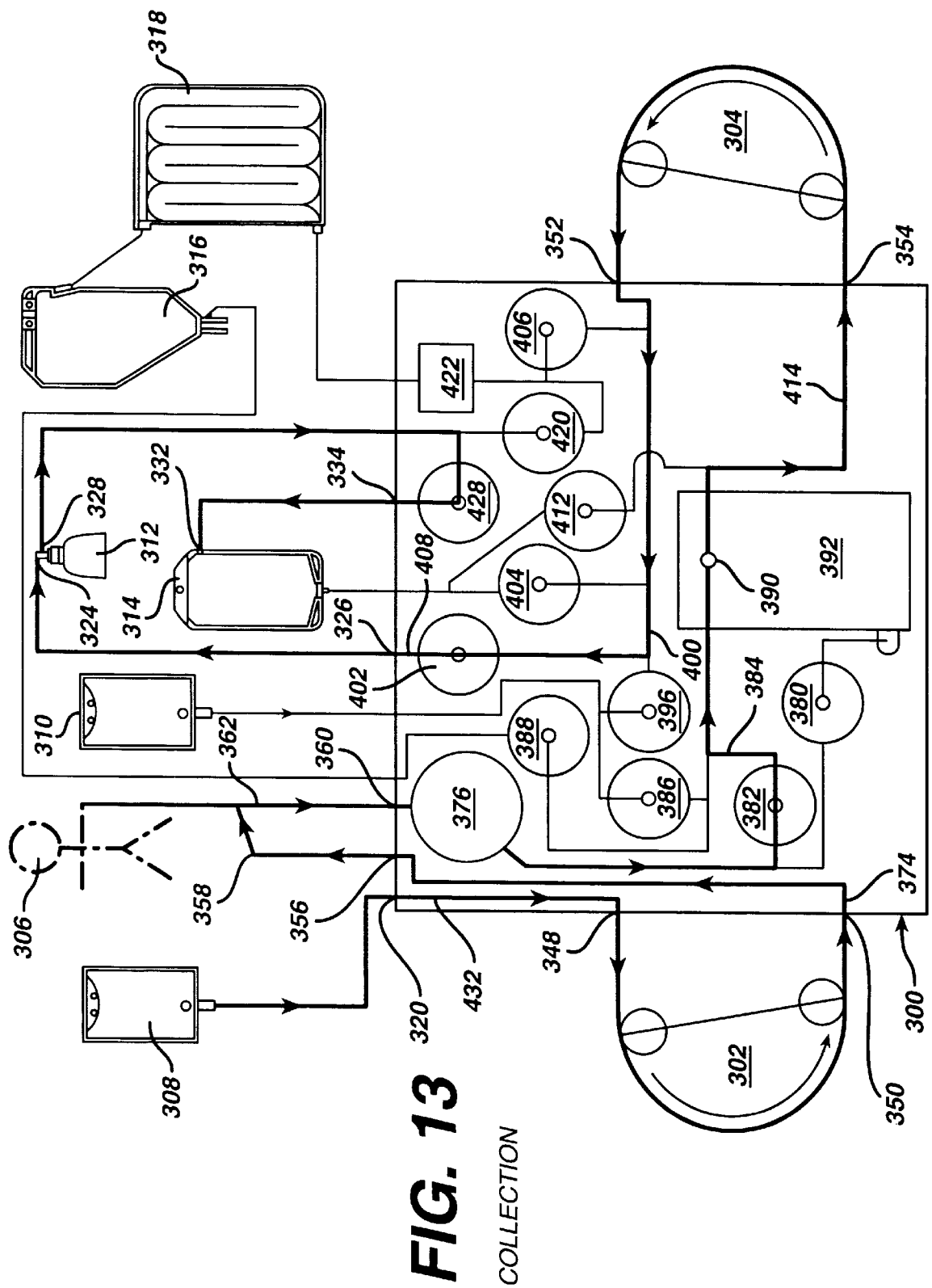
Figure 14:
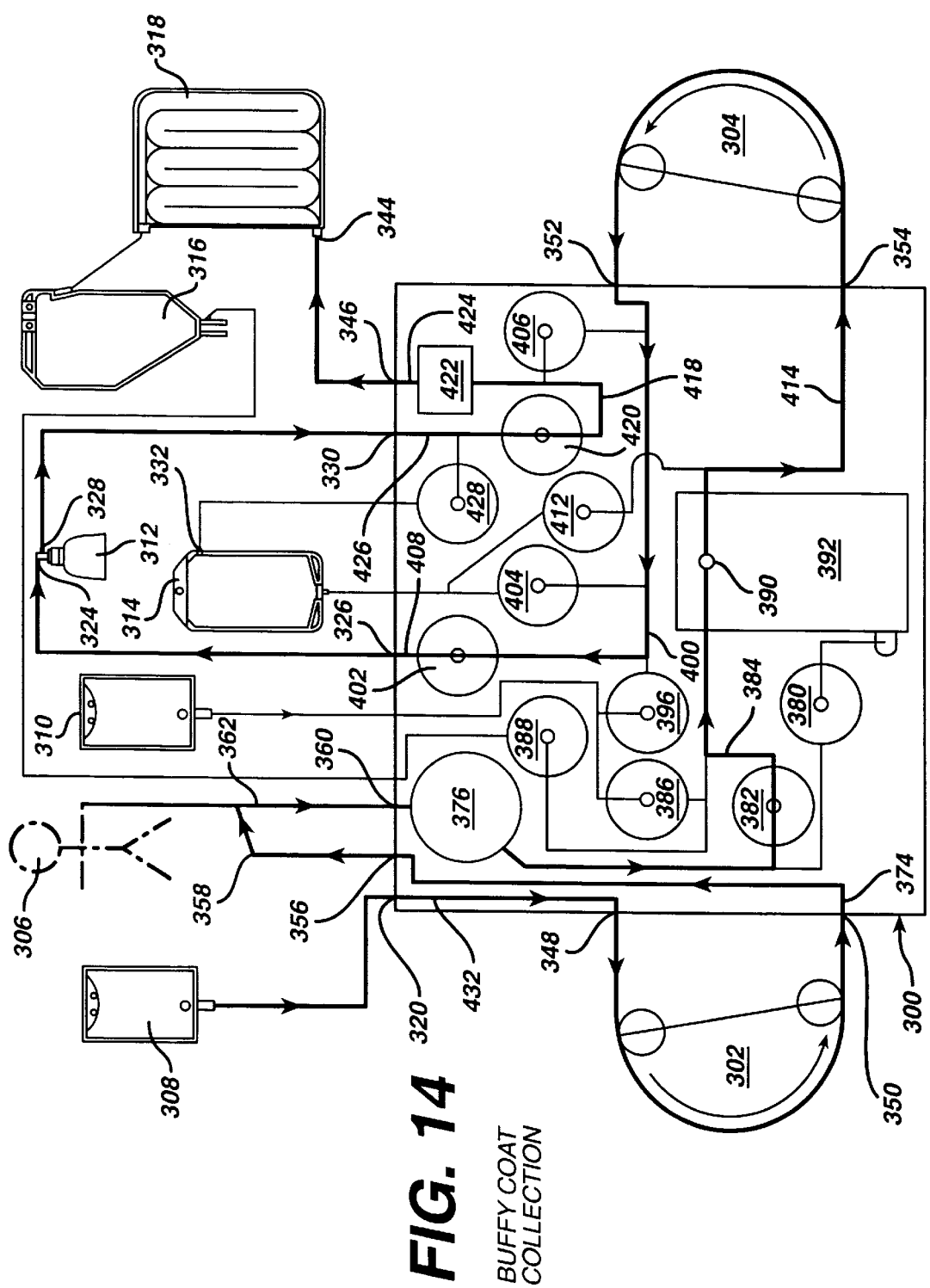
Figure 15:
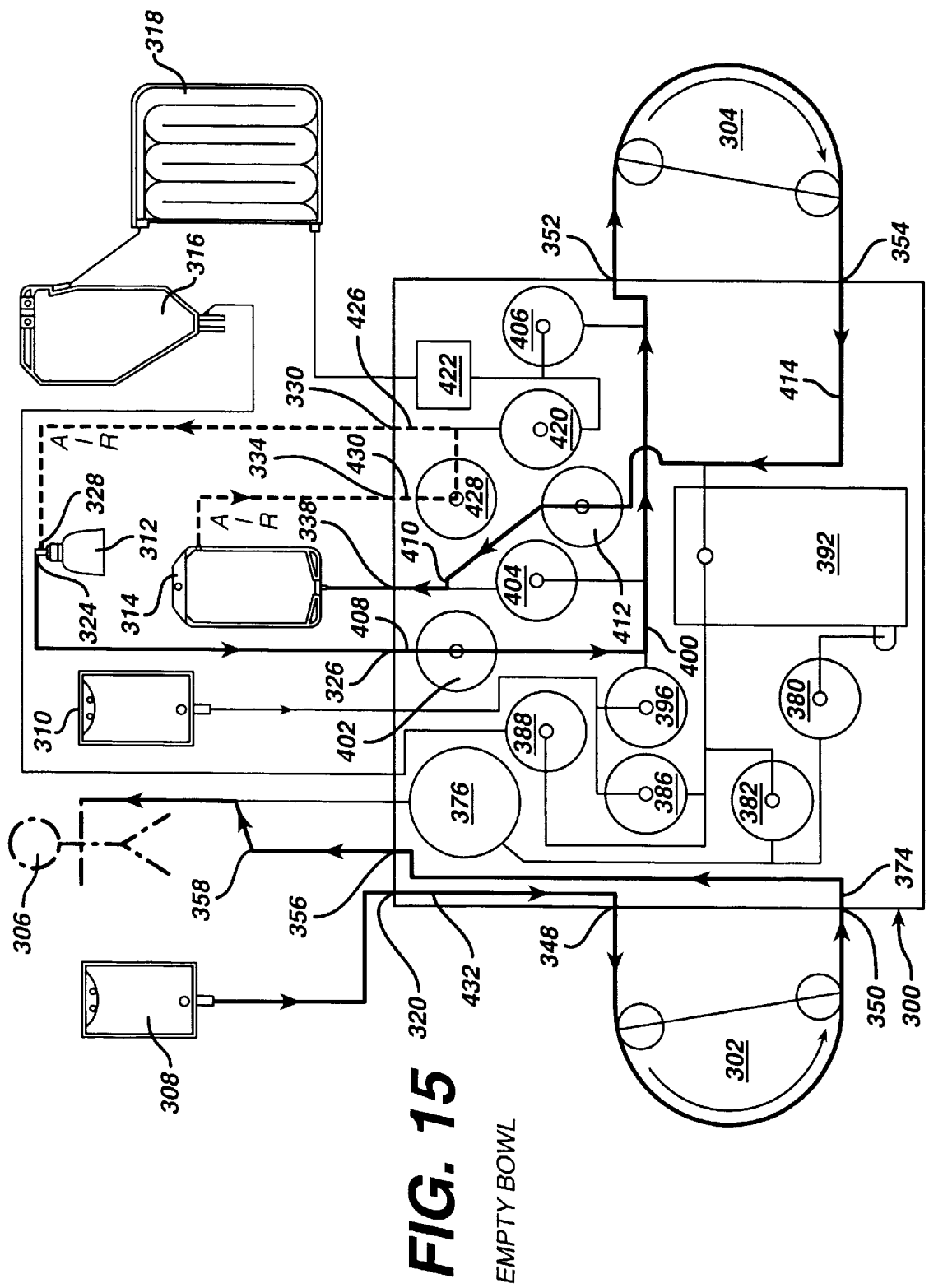
Figure 16:
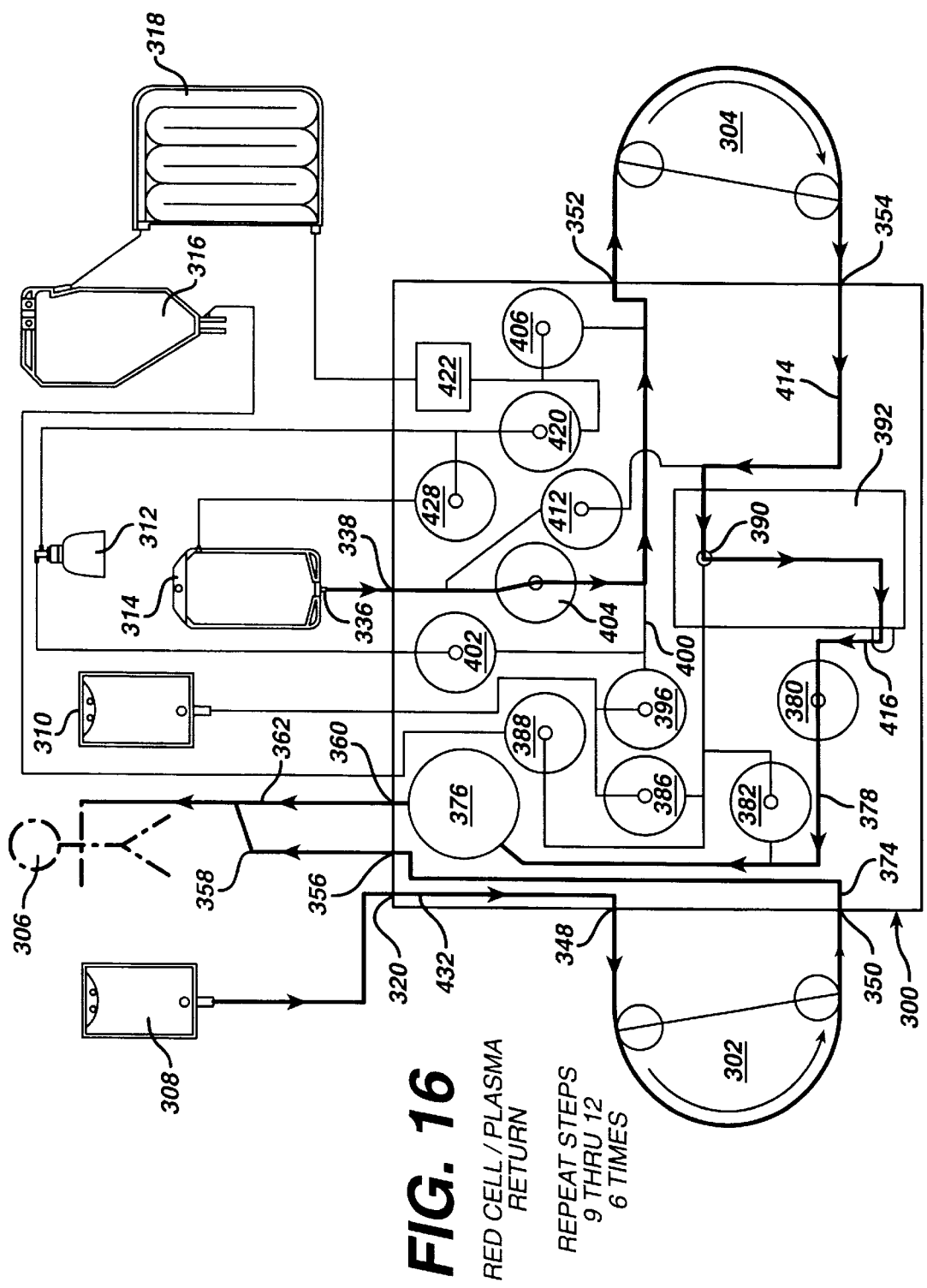
Figure 17:
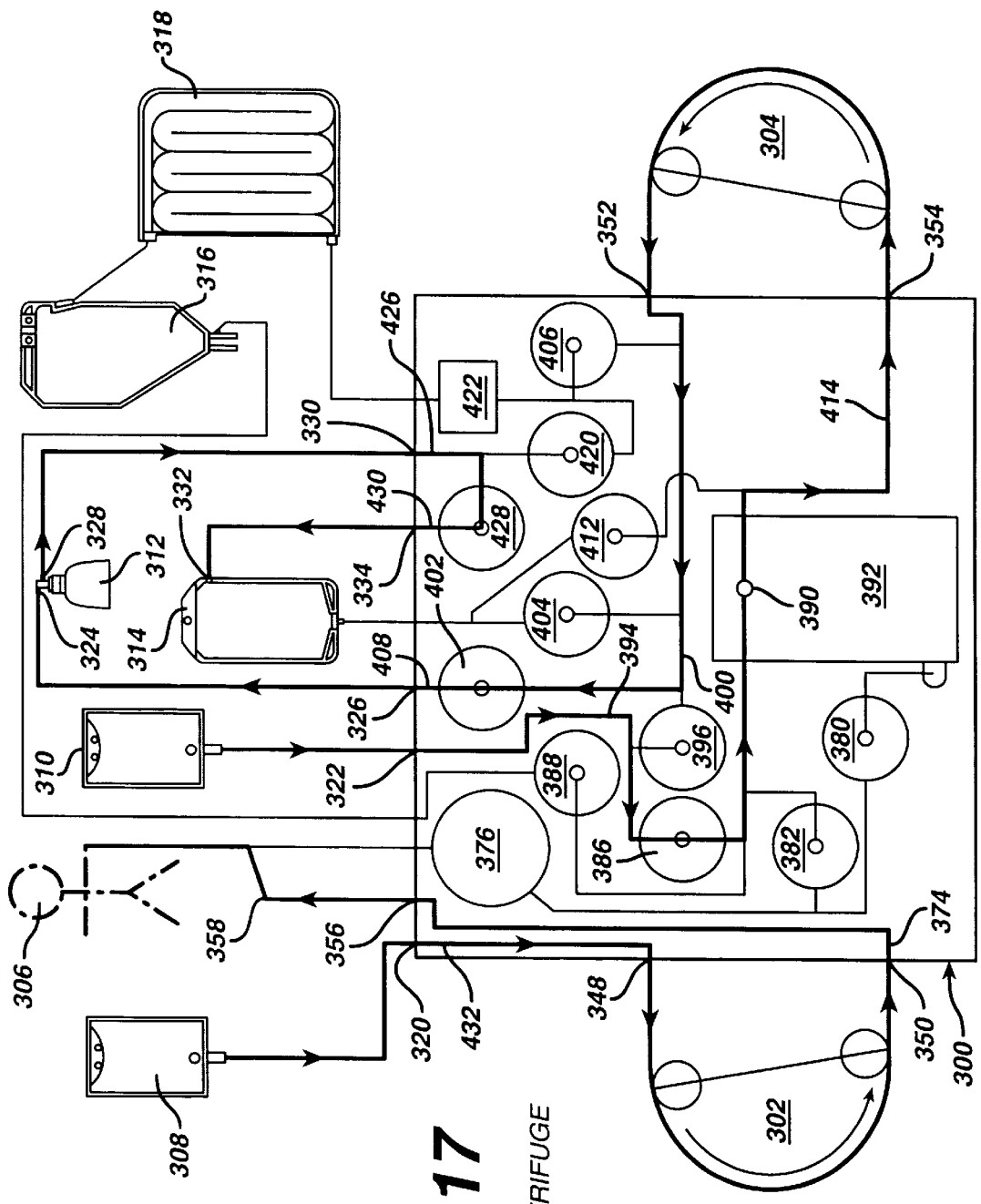
Figure 18:
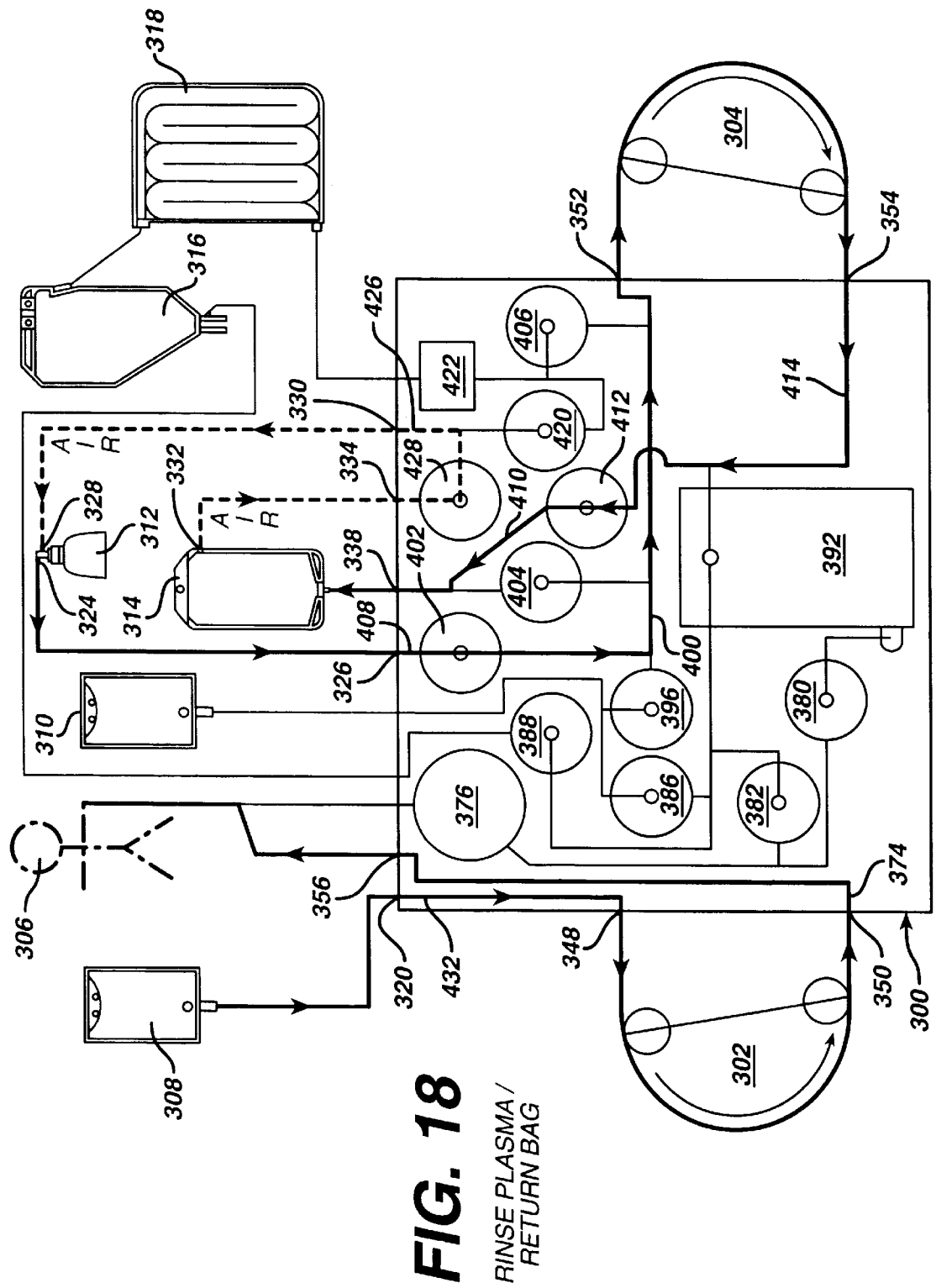
Figure 19:
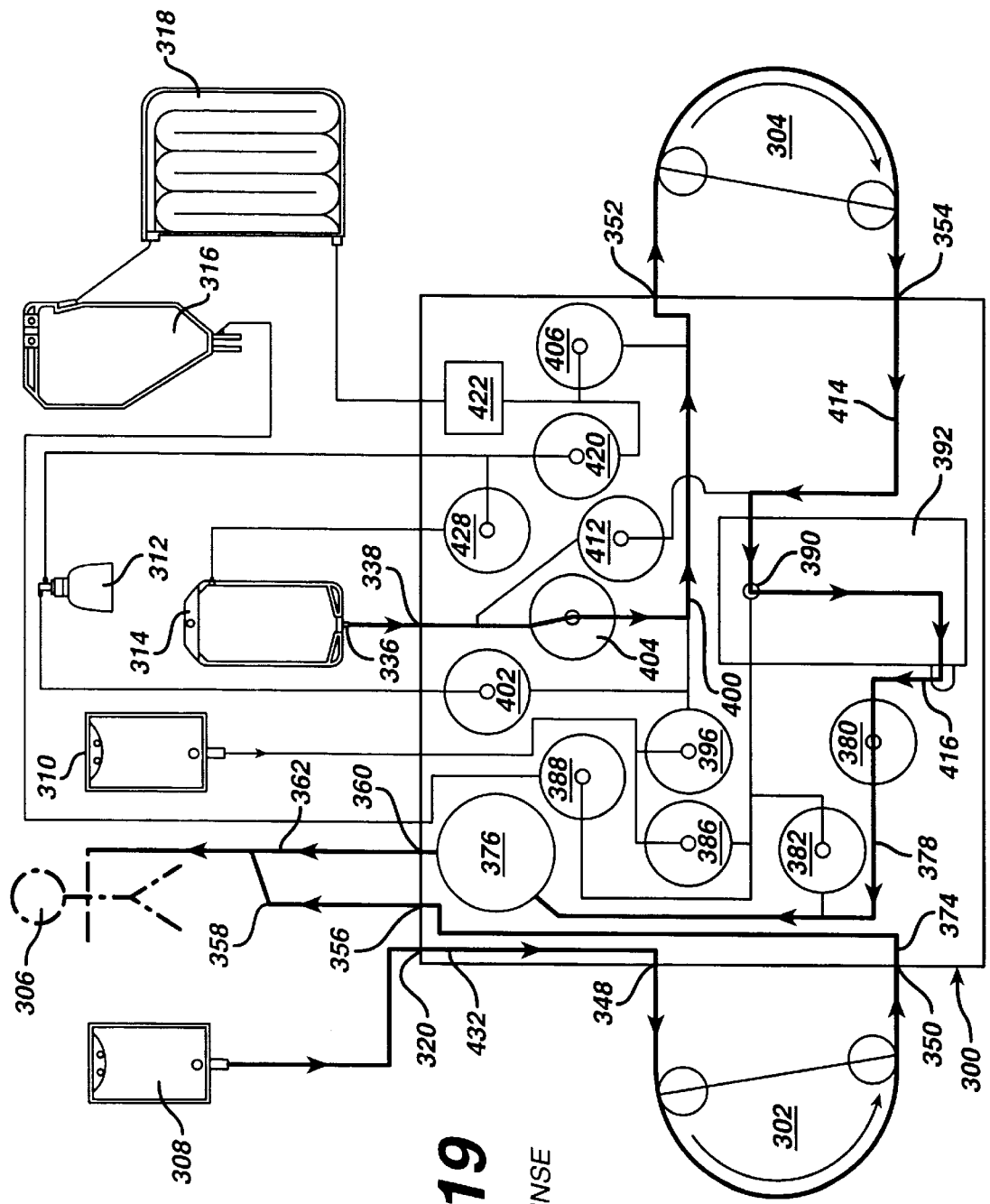
Figure 20:
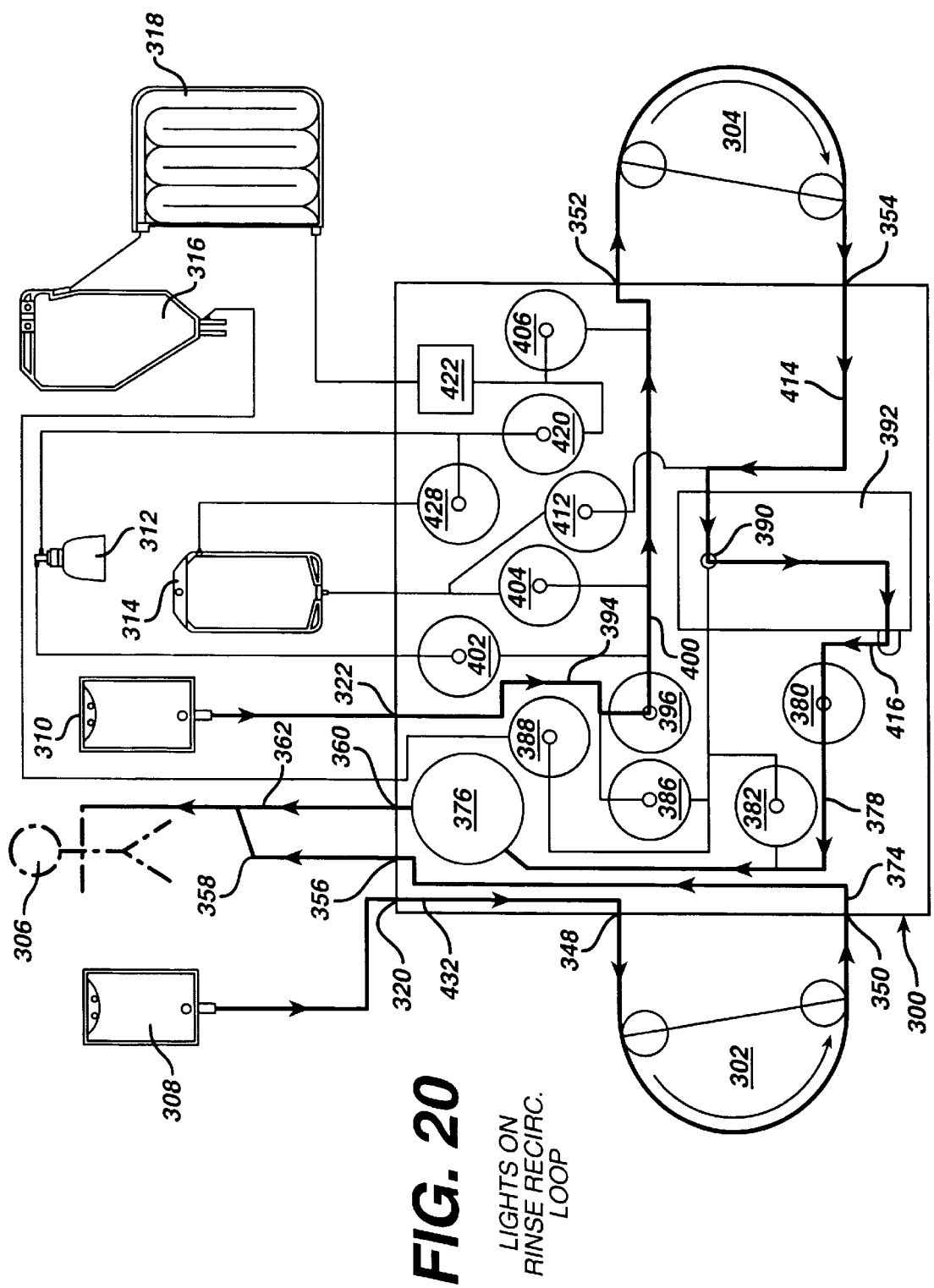

FIGS. 5 through 27 depicts various stages in a treatment employing the cassette 300, with the dark lines and arrows indicating flows within the cassette 300. FIGS. 5 to 12 depict the initial priming stages wherein air is displaced from the systems and replaced with fluid. FIG. 13 shows blood collection commencing with the clamp 364 removed from the patient line 362. During in step plasma is being separated from the whole body the separator 312 and is passed into the plasma collection 314. A detector (not shown) for red blood within the separator 312 in connection with a timing delay sets the cassette 300 into the configuration of FIG. 14 as the last of the plasma is leaving the separator 362. First, some plasma, and then the buffy coat or white blood cells pass through the hematocrit detector 422 and into the treatment chamber. When the hematocrit detector 422 detects the final blood fraction, the red blood cells, it sets the cassette into the orientation of FIG. 15 so as to empty any blood remaining in the separator 312 into the plasma collection bag 314. The plasma is then returned to the patient 306 as shown in FIG. 16. The steps shown in FIGS. 13 to 16 are typically repeated for about six times to amass sufficient white blood cells within the treatment chamber 318.

Figure 21:
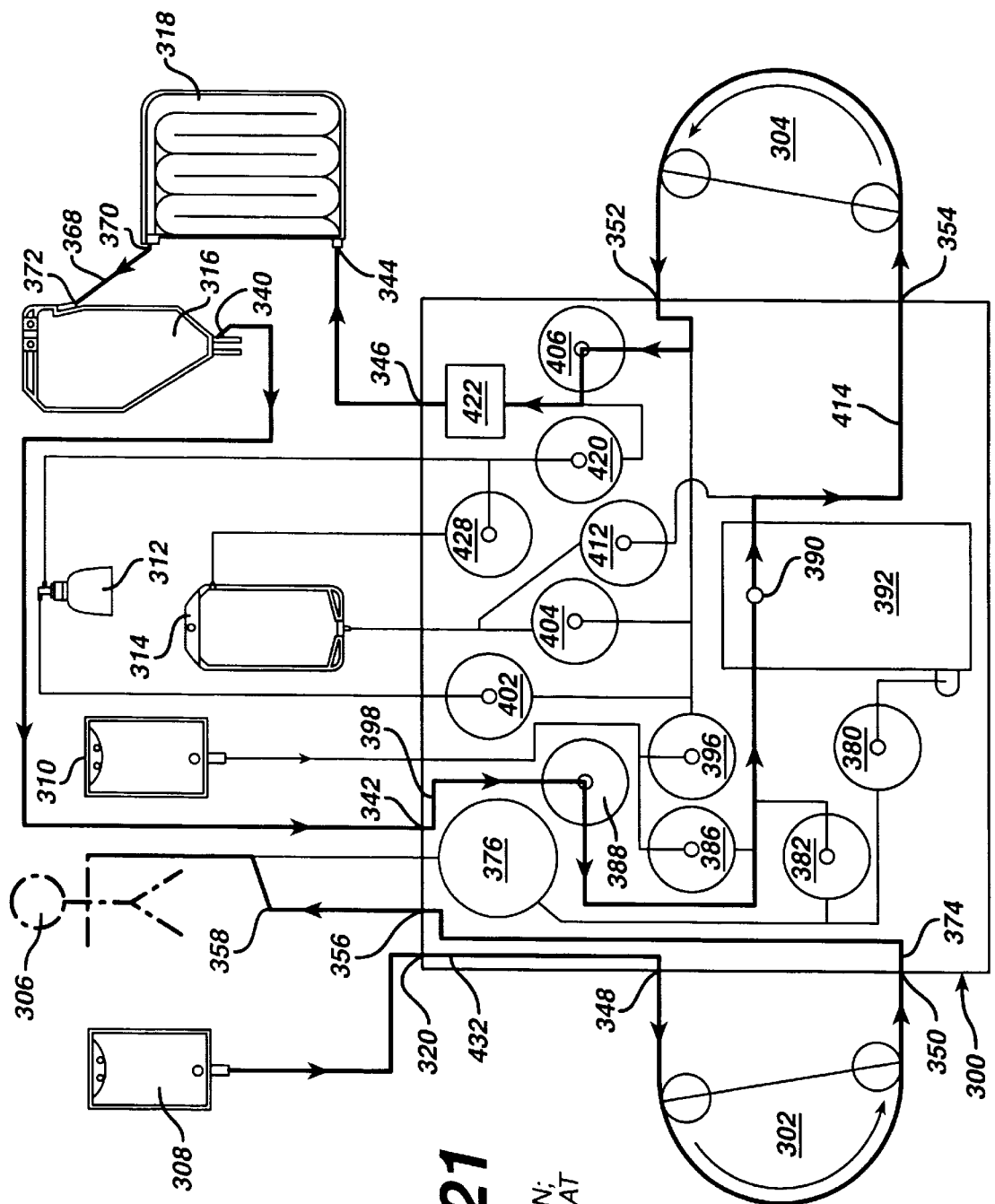
Figure 22:
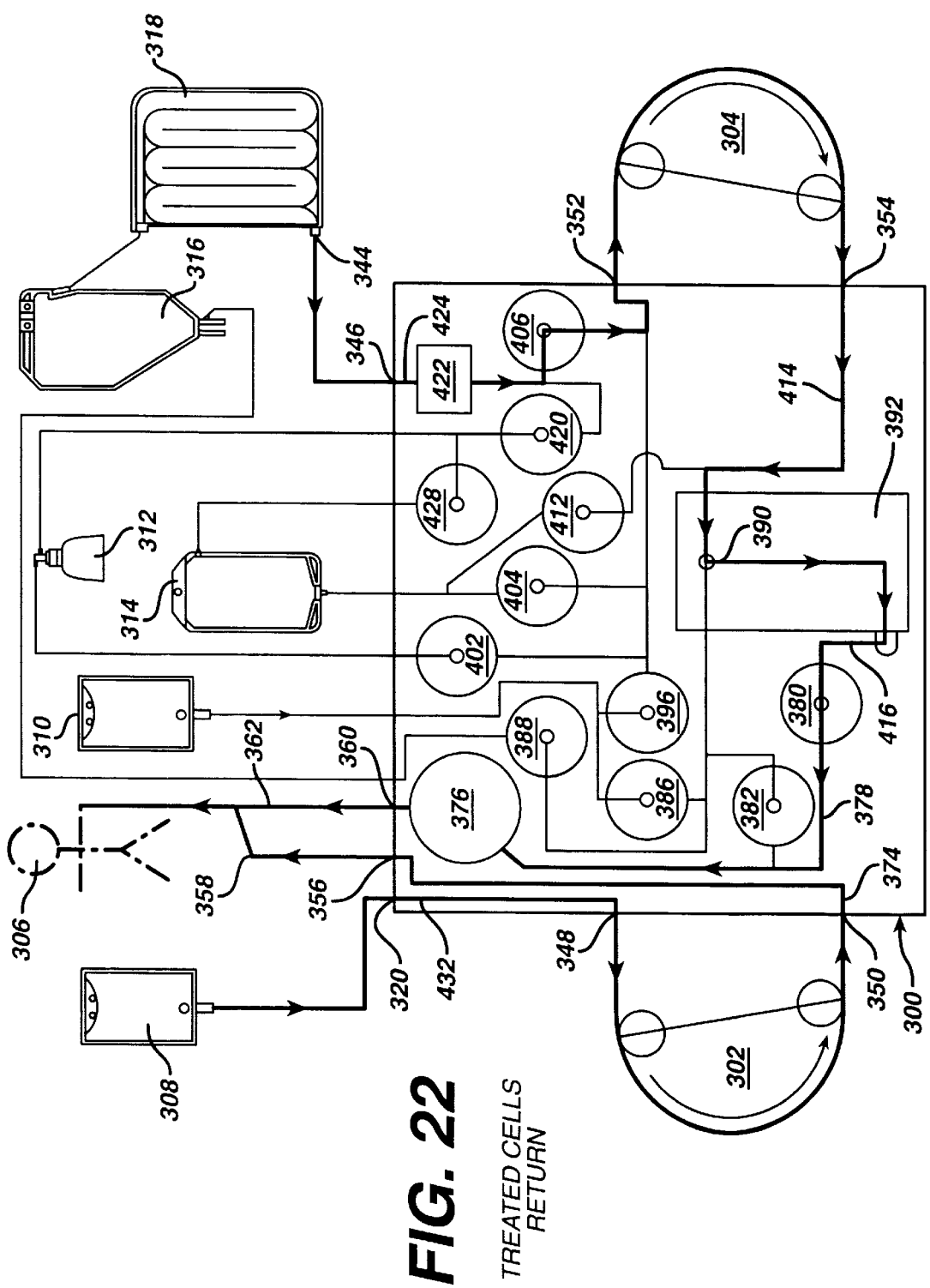
Figure 23:
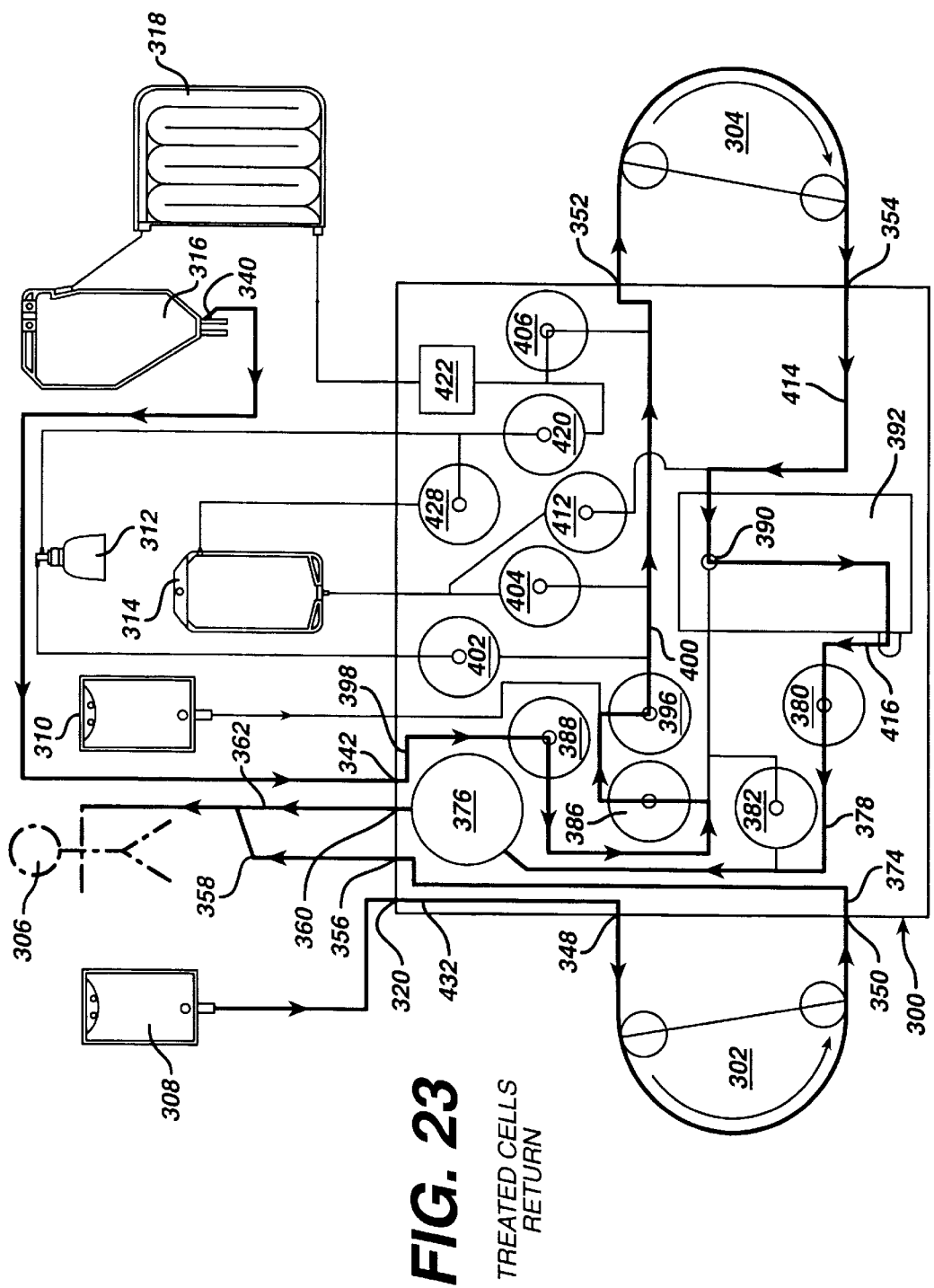
Figure 24:
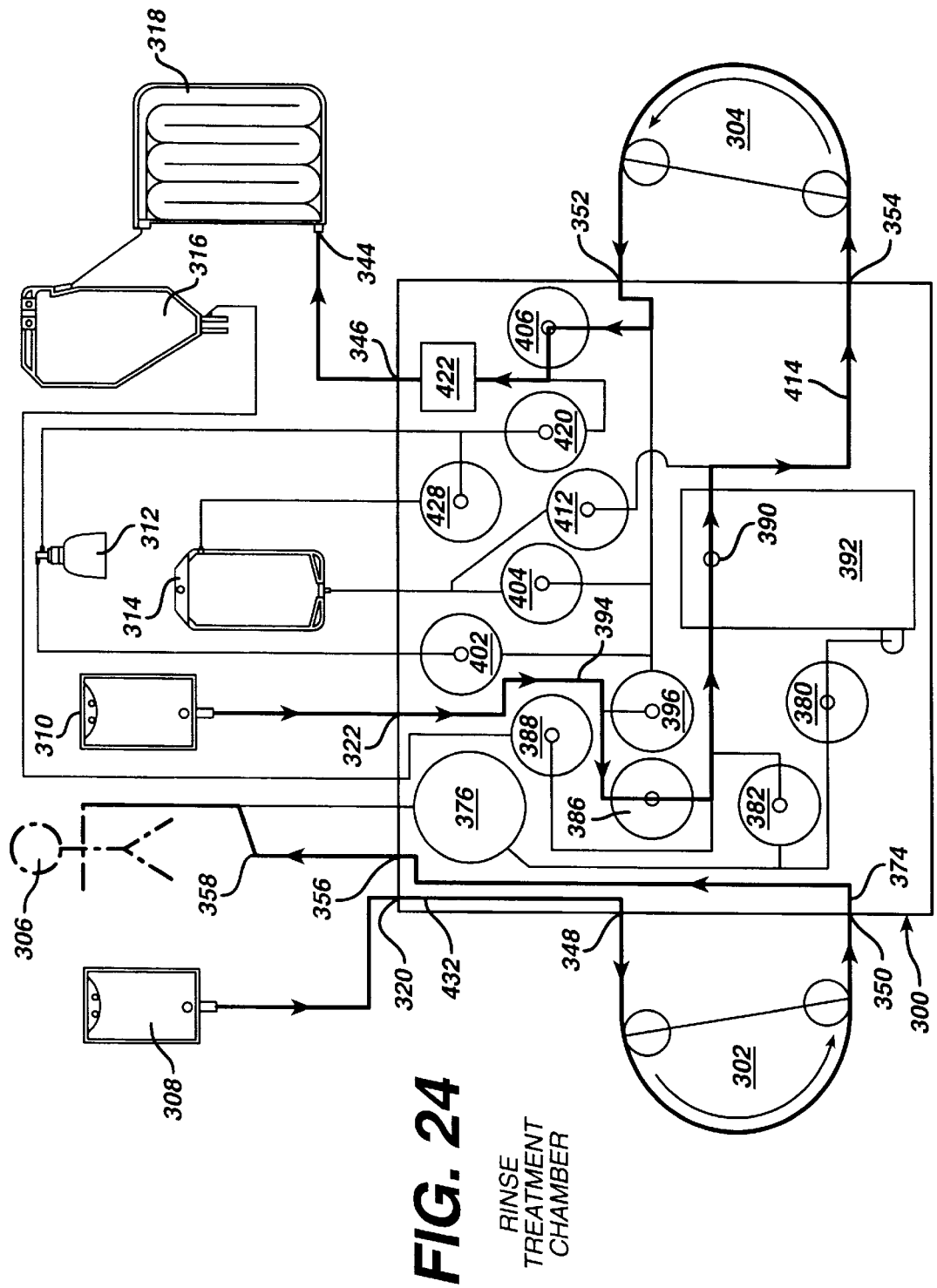
Figure 25:
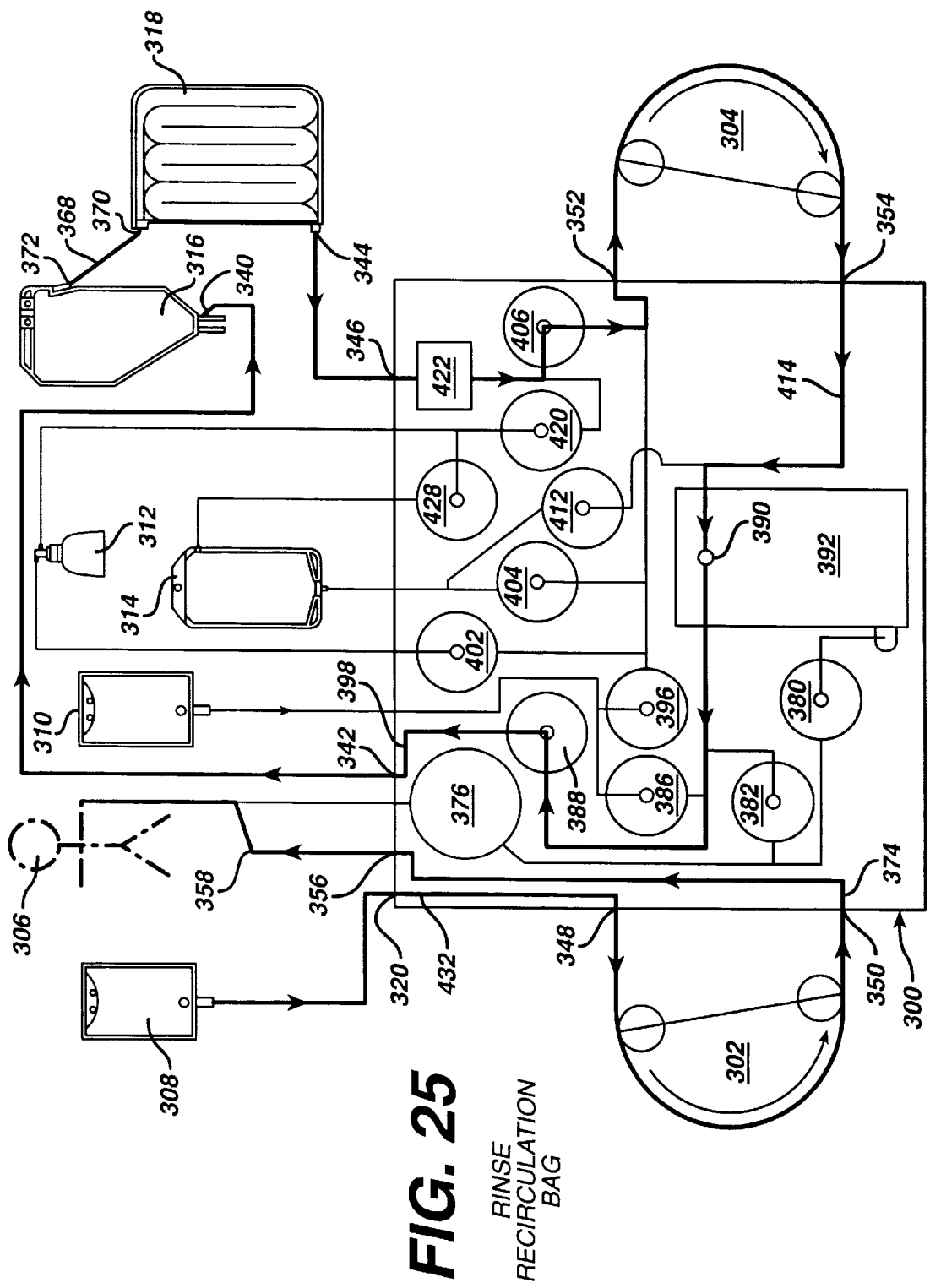
Figure 26:
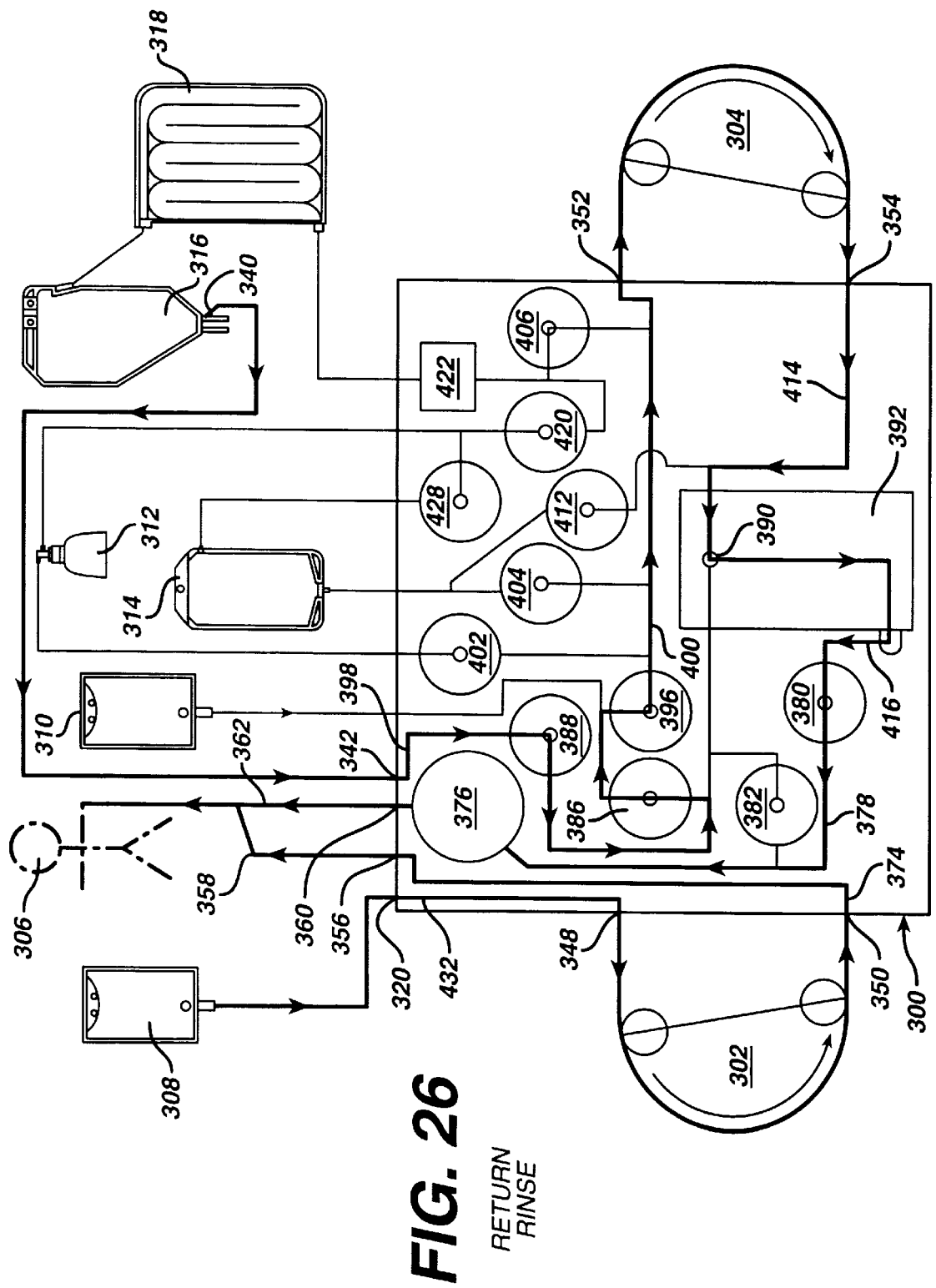
Figure 27:
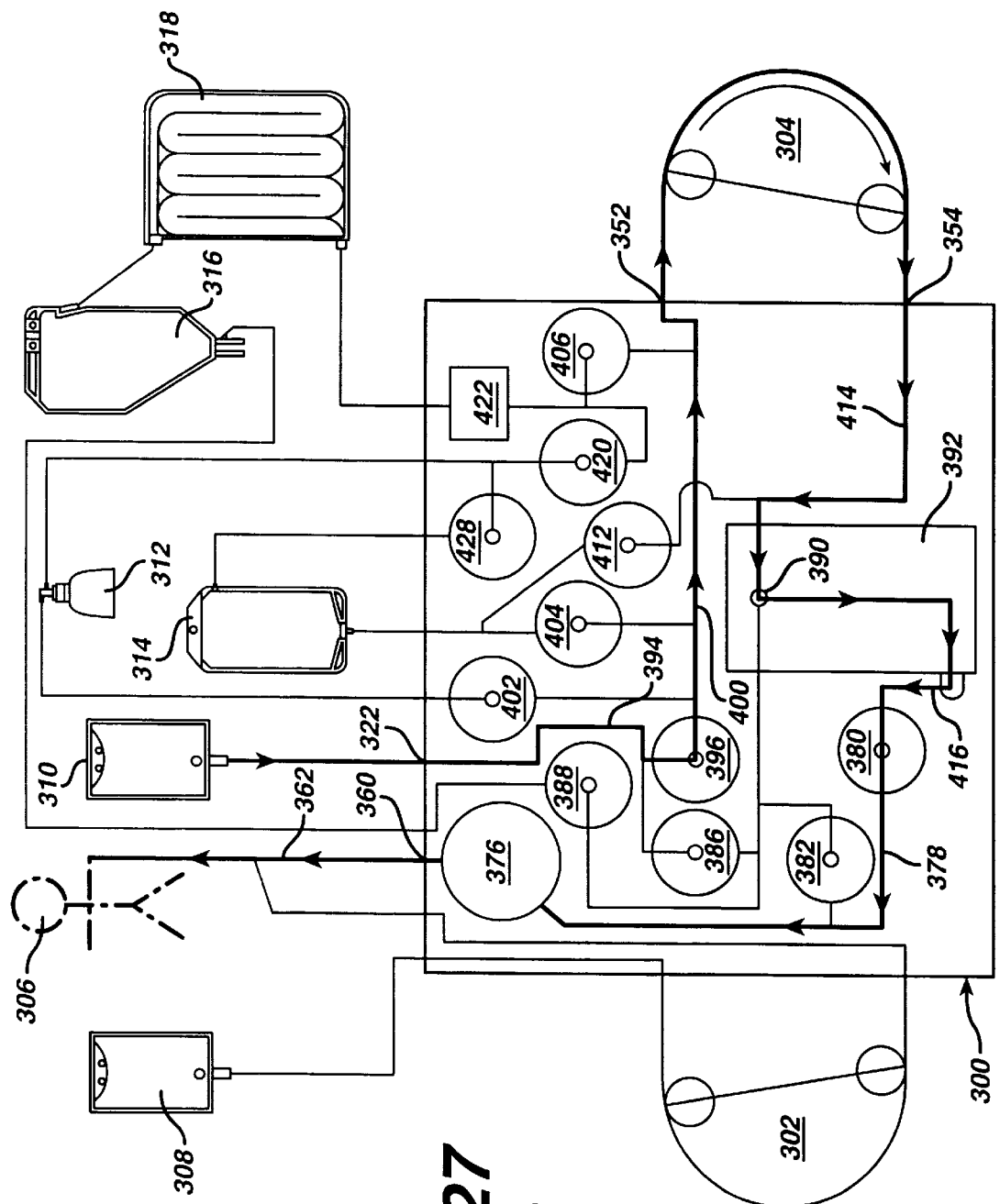

FIGS. 17 to 20 depict rinsing steps, and by the final rinsing step the lights (not shown) to the treatment chamber 318 are turned on to begin treating the white blood cells therein. FIG. 21 depicts how the white blood cells are recirculated through the treatment chamber 318. FIGS. 22 and 23 depict the return of the treated cells to the patient 306 and FIGS. 24 to 26 depict the final rinsing and return to the patient of blood from the cassette 300. Finally, saline from the saline bag 310 is supplied to the patient as shown in FIG. 27.

Figure 28:
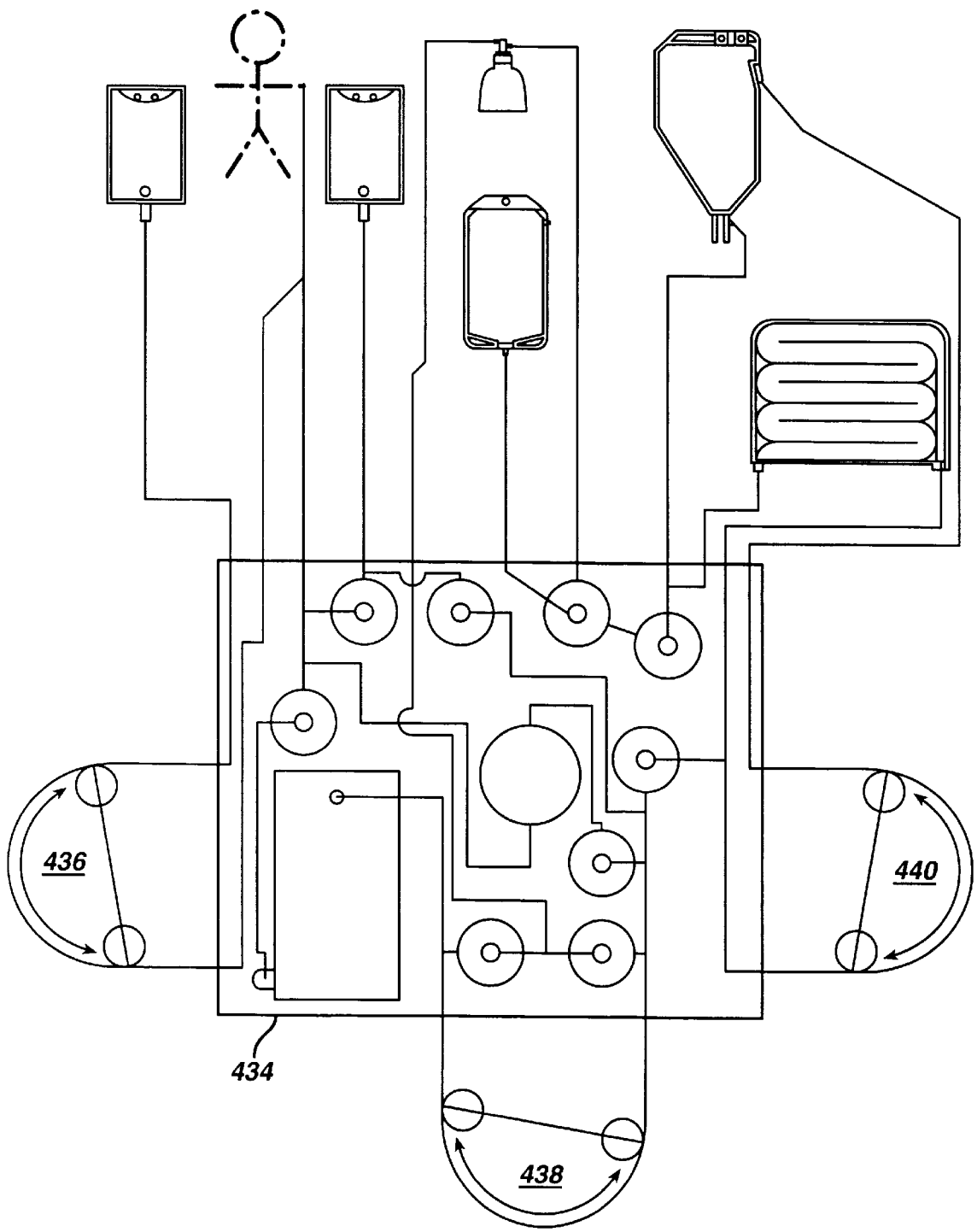
FIG. 28 shows in schematic form a further embodiment of an extracorporeal blood treatment system according to the invention.

FIG. 28 shows how a cassette 434 can be provided employing three roller pumps, including an anticoagulant pump 436, a blood pump 438 and a recirculation pump 440. Having the dedicated recirculation pump 440 allows a cycle to be run whereby white blood cells circulate through the treatment chamber even as plasma is being returned to the patient. In FIGS. 5 to 27 the recirculation could not begin until the blood pump 304 was free to be dedicated to that task.

Figure 29:
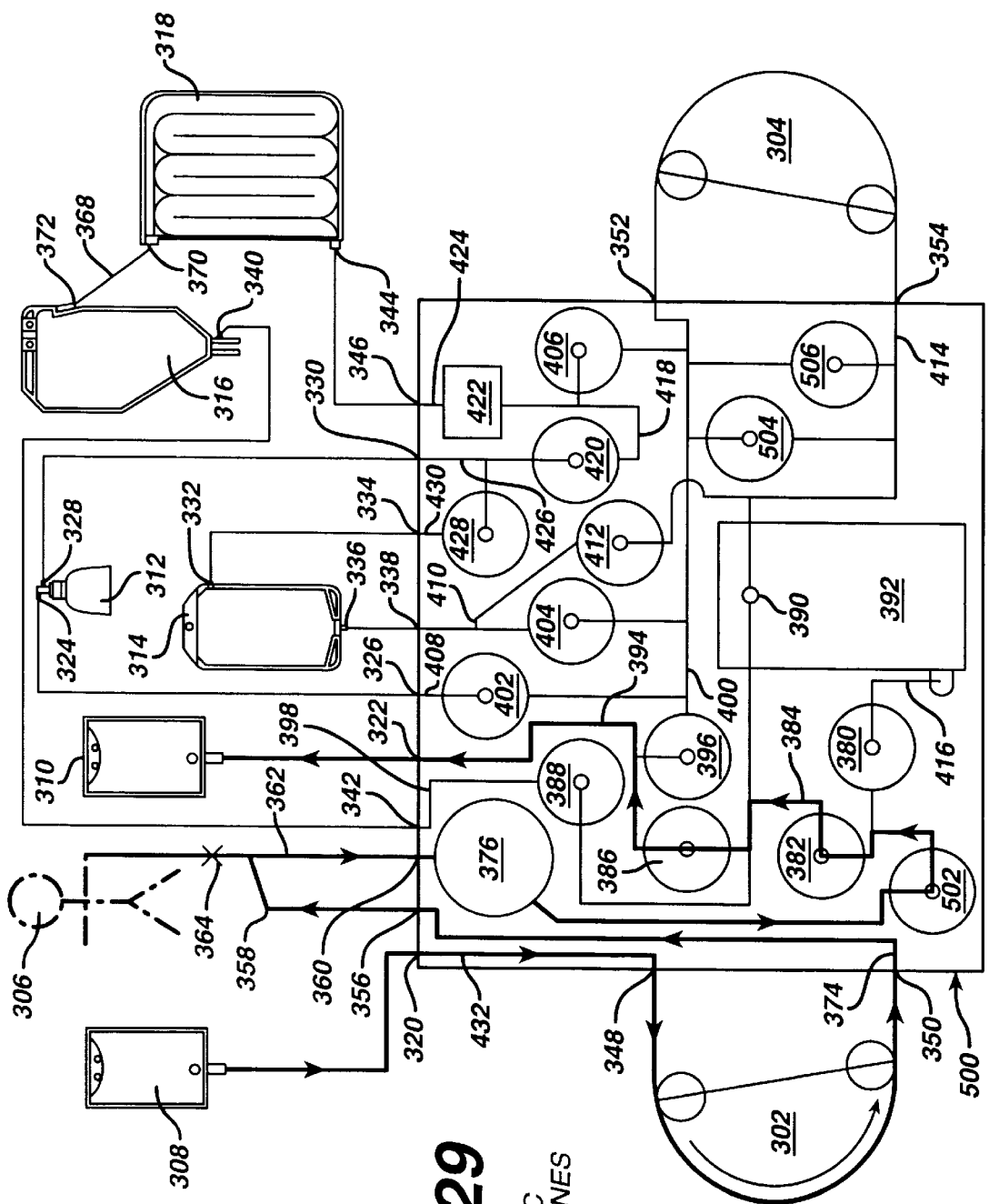
FIG. 29 shows in schematic form a further embodiment of an extracorporeal blood treatment system according to the invention incorporating novel negative pressure and pressure relief valves.

FIG. 29 depicts a cassette 500 essentially identical to cassette 300 with the addition of a negative pressure valve 502 into passage 378 and a pair of pressure relief valves 504 and 506 across the ports 352 and 354 of the blood pump 304. The negative pressure valve 502 prevents excessive negative pressure in the passage 378 in communication with the patient line 362. The pressure relief valves 504 and 506 prevent overpressure in the blood pump 304 by recirculating flow through the pump 304 in such an event.

Figure 30:
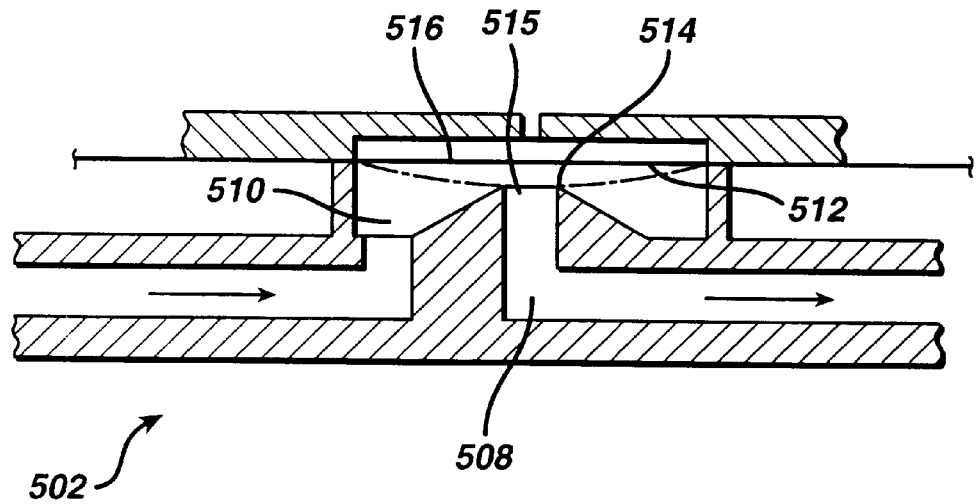
FIG. 30 is a cross sectional view through the negative pressure valve of FIG. 29.

FIG. 30 shows a sectional view through the negative pressure valve 502. Its construction is similar to that of the other membrane valves on the cassette 500, having an outlet passage 508 terminating in a valve inlet chamber 510 which is at least partly defined by a flexible membrane 512. Contact between the membrane 512 and a sealing lip 514 at an opening 515 at the termination of the passage 508 into the chamber 510 prevents flow through the valve 502. However, in the negative pressure valve 502, the flow is reversed with flow coming into to chamber 510 and exiting through the passage 508. Thus, if too much flow is drawn by the pump 304 creating a negative pressure at the valve chamber 510, the membrane will be drawn to the lip 514. The membrane 512 is biased so as to close the valve 502 at a predetermined negative pressure. The membrane 512 can be biased in many ways, such as by stretching the membrane 512, by applying a reference fluid pressure to an opposite side 516 thereof, biasing the membrane 51 with a spring, elastomeric member or other known biasing methods as will be apparent to those of skill in the art. Further, while the valve 502 comprises a preferred method of forming a negative pressure valve other known expedients, such as commercially available pressure valves, may be substituted therefor as will be apparent to hose of skill in the art.

Figure 31:
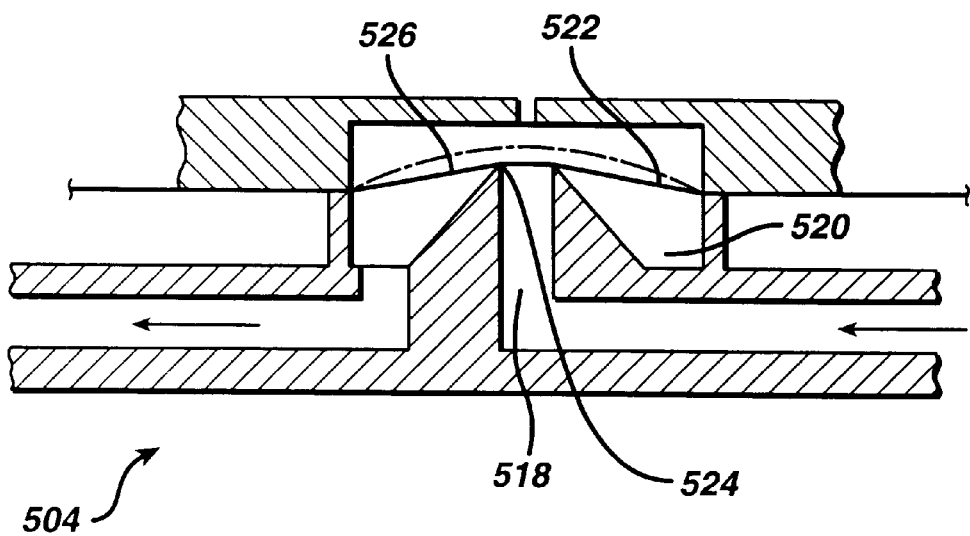
FIG. 31 is a cross sectional view through the one of the pressure relief valves of FIG. 29.

FIG. 31 shows a sectional view through one of the pressure relief valves 504 and 506. The positive pressure relief valves are similarly structured, with an inlet passage 518 terminating in a valve chamber 520 which is partly defined by a membrane 522. Here, flow is in the normal direction, but the membrane 522 normally rests against a lip 524 at the termination of the inlet passage 518 so as to hold the valve normally closed. Again, the membrane is biased, such as by stretching or through application of a reference pressure to an opposite side 526 thereof. When pressure in the inlet passage 518 is sufficient to overcome the bias on the membrane 522 the membrane lifts away from the lip 524 allowing flow through the valve 504 or 506 and back through the pump 304. While valves 504 and 506 represent a certain preferred embodiment, other biasing means and pressure relief valving may be substituted therefor as will be apparent to those of skill in the art.

Figure 32:
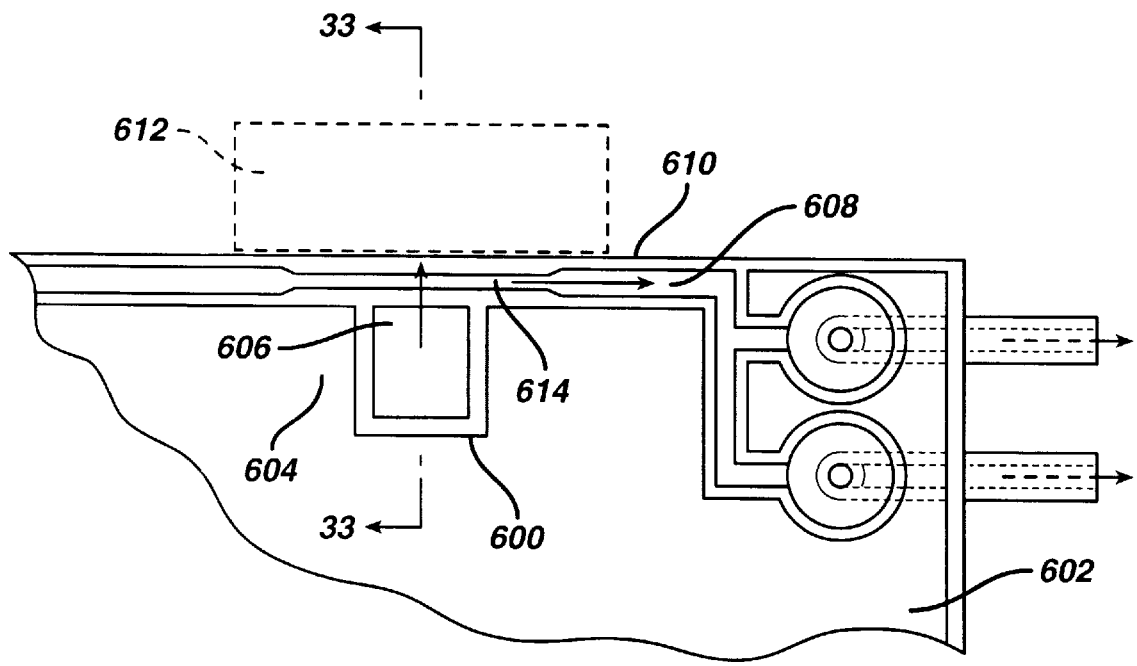
FIG. 32 is a plan view of a hematocrit detection window in a cassette according to the invention.
Figure 33:
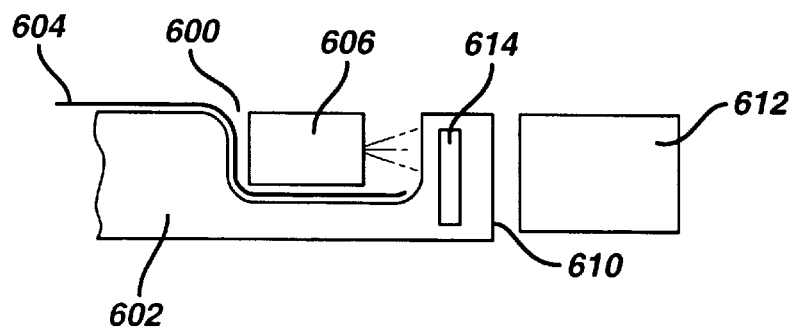
FIG. 33 is a cross sectional view taken along lines 33—33 of FIG. 32.

FIGS. 32 and 33 depict a preferred manner of detecting hematocrits. A recessed area 600 is provided in a cassette 602 and membrane 604. The membrane 604 is attached to the cassette 602 at the recessed area 600, rather than being loose. This allows a light emitting diode (LED) 606 or other light source to fit within the recessed area 600 and shine light through a passage 608 at an outside edge 610 of the cassette 602. A photodetector 612 is positioned adjacent the cassette outside edge 610 at this point to monitor the light coming from the LED 606. Red blood cells absorb much more light than plasma or white blood cells so that as the components change in the passage 608 the decreased light reaching the photodetector 612 indicates the presence of red blood cells. Preferably, the passage 608 narrows and becomes taller creating an efficient window 614 through which to shine light from the LED 606.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. An apparatus for controlling movement of fluids during an extracorporeal blood treatment session, comprising:
a hollow enclosure having a plurality of fluid input ports for receiving said fluids into said enclosure and a plurality of fluid output ports for expelling said fluids from said enclosure;
internal fluid passageways disposed within said hollow enclosure for coupling together said fluid input ports, and said fluid output ports;
at least one internal valve disposed within said hollow enclosure and connected to at least one of said internal fluid passageways for controlling movement of said fluid within said hollow enclosure during said extracorporeal blood treatment session;
a filter in said hollow enclosure and connected to at least one of said internal fluid passageways for filtering said fluid, and wherein said filter is adapted to pass whole blood and filter blood clots therefrom; and
wherein said filter comprises a first chamber and a second chamber within the enclosure which are separated from each other by a filter media.

2. The apparatus of claim 1 wherein the filter media comprises a woven mesh.

3. The apparatus of claim 2 wherein the woven mesh comprises a polyester.

4. The apparatus of claim 1 wherein said first chamber is at least partially formed of a first layer of elastomeric membrane material disposed on a first outer surfaces of said hollow enclosure.

5. An apparatus for controlling movement of fluids during an extracorporeal blood treatment session, comprising:
a hollow enclosure having a plurality of fluid input ports for receiving said fluids into said enclosure and a plurality of fluid output ports for expelling said fluids from said enclosure;
internal fluid passageways disposed within said hollow enclosure for coupling together said fluid input ports, and said fluid output ports;
at least one internal valve disposed within said hollow enclosure and connected to at least one of said internal fluid passageways for controlling movement of said fluid within said hollow enclosure during said extracorporeal blood treatment session; and
a filter in said hollow enclosure and connected to at least one of said internal fluid passageways for filtering said fluid, and wherein said filter is adapted to pass whole blood and filter blood clots therefrom.

6. An apparatus for controlling movement of fluids during an extracorporeal blood treatment session, comprising:

a hollow enclosure having a plurality of fluid input ports for receiving said fluids into said enclosure and a plurality of fluid output ports for expelling said fluids from said enclosure;

internal fluid passageways disposed within said hollow enclosure for coupling together said fluid input ports, and said fluid output ports;

at least one internal valve disposed within said hollow enclosure and connected to at least one of said internal fluid passageways for controlling movement of said fluid within said hollow enclosure during said extracorporeal blood treatment session; and a filter in said hollow enclosure and connected to at least one of said internal fluid passageways for filtering said fluid, and wherein said filter is adapted to filter blood clots from whole blood, wherein said filter comprises a first chamber and a second chamber within the enclosure which are separated from each other by a filter media, and wherein the filter media comprises a mesh having a pore size of about 200 microns.

7. An apparatus for controlling movement of fluids during an extracorporeal blood treatment session, comprising:

a hollow enclosure having a plurality of fluid input ports for receiving said fluids into said enclosure and a plurality of fluid output ports for expelling said fluids from said enclosure;

internal fluid passageways disposed within said hollow enclosure for coupling together said fluid input ports, and said fluid output ports;

at least one internal valve disposed within said hollow enclosure and connected to at least one of said internal fluid passageways for controlling movement of said fluid within said hollow enclosure during said extracorporeal blood treatment session; and a filter in said hollow enclosure and connected to at least one of said internal fluid passageways for filtering said fluid, and wherein said filter is adapted to filter blood clots from whole blood, wherein said filter comprises a first chamber and a second chamber within the enclosure which are separated from each other by a filter media, and wherein the filter media comprises a mesh having a pore size between about 200 microns and about 400 microns.

8. An apparatus for controlling movement of fluids during an extracorporeal blood treatment session, comprising:

a hollow enclosure having a plurality of fluid input ports for receiving said fluids into said enclosure and a plurality of fluid output ports for expelling said fluids from said enclosure;

internal fluid passageways disposed within said hollow enclosure for coupling together said fluid input ports, and said fluid output ports;

at least one internal valve disposed within said hollow enclosure and connected to at least one of said internal fluid passageways for controlling movement of said fluid within said hollow enclosure during said extracorporeal blood treatment session;

a filter in said hollow enclosure and connected to at least one of said internal fluid passageways for filtering said fluid, and wherein said filter is adapted to filter blood clots from whole blood, wherein said filter comprises a first chamber and a second chamber within the enclosure which are separated from each other by a filter media; and air evacuation means for evacuating air from at least one of said first and second chambers.

9. An apparatus for controlling movement of fluids during an extracorporeal blood treatment session, comprising:

a hollow enclosure having a plurality of fluid input ports for receiving said fluids into said enclosure and a plurality of fluid output ports for expelling said fluids from said enclosure;

internal fluid passageways disposed within said hollow enclosure for coupling together said fluid input ports, and said fluid output ports;

at least one internal valve disposed within said hollow enclosure and connected to at least one of said internal fluid passageways for controlling movement of said fluid within said hollow enclosure during said extracorporeal blood treatment session;

a filter in said hollow enclosure and connected to at least one of said internal fluid passageways for filtering said fluid, and wherein said filter is adapted to filter blood clots from whole blood, wherein said filter comprises a first chamber and a second chamber within the enclosure which are separated from each other by a filter media; and a second filter in said hollow enclosure.

* * * * *